(12) United States Patent
Ganesan

(10) Patent No.: US 6,774,628 B2
(45) Date of Patent: Aug. 10, 2004

(54) NUCLEAR MAGNETIC RESONANCE IMAGING USING PHASE ENCODING WITH NON-LINEAR GRADIENT FIELDS

(75) Inventor: Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 35 days.

(21) Appl. No.: 10/051,479

(22) Filed: Jan. 18, 2002

(65) Prior Publication Data

US 2003/0137297 A1 Jul. 24, 2003

(51) Int. Cl.⁷ ................................................ G01V 3/00
(52) U.S. Cl. ........................................................ 324/303
(58) Field of Search ........................................ 324/303

(56) References Cited

U.S. PATENT DOCUMENTS

| | | | |
|---|---|---|---|
| 4,717,878 A | 1/1988 | Taicher et al. | 324/303 |
| 5,055,787 A | 10/1991 | Kleinberg et al. | 324/303 |
| 5,212,447 A | 5/1993 | Paltiel | 324/300 |
| 5,280,243 A | 1/1994 | Miller | 324/303 |
| 5,345,176 A | 9/1994 | LeRoux et al. | |
| 5,410,249 A | 4/1995 | Van Yperen et al. | |
| 5,428,291 A * | 6/1995 | Thomann et al. | 324/303 |
| 5,473,158 A | 12/1995 | Holenka et al. | 250/254 |
| 5,565,775 A * | 10/1996 | Stallmach et al. | 324/303 |
| 5,629,623 A | 5/1997 | Sezginer et al. | |
| 5,696,448 A * | 12/1997 | Coates et al. | 324/303 |
| 5,757,186 A | 5/1998 | Taicher et al. | 324/303 |
| 5,796,252 A | 8/1998 | Kleinberg et al. | 324/303 |
| 5,892,460 A | 4/1999 | Jerabek et al. | 340/856.4 |
| 5,914,598 A | 6/1999 | Sezginer et al. | |
| 5,977,768 A | 11/1999 | Sezginer et al. | 324/303 |
| 6,018,243 A | 1/2000 | Taicher et al. | 324/303 |
| 6,111,408 A | 8/2000 | Blades et al. | 324/303 |
| 6,121,773 A | 9/2000 | Taicher et al. | 324/303 |
| 6,147,489 A * | 11/2000 | Freedman et al. | 324/303 |
| 6,166,540 A * | 12/2000 | Wollin | 324/300 |
| 6,181,138 B1 | 1/2001 | Hagiwara et al. | 324/338 |
| 6,232,778 B1 | 5/2001 | Speier et al. | |
| 6,237,404 B1 | 5/2001 | Crary et al. | |
| 6,246,236 B1 | 6/2001 | Poitzsch et al. | 324/303 |

(List continued on next page.)

FOREIGN PATENT DOCUMENTS

| | | |
|---|---|---|
| EP | 0 675 372 A1 | 10/1995 |
| WO | WO01/46549 A1 | 6/2001 |
| WO | WO 03/040743 A1 | 5/2003 |

OTHER PUBLICATIONS

Kenyon et al., *Nuclear Magnetic Resonance Imaging—Technology for the 21$^{st}$ Century*, CPMG Pulse Sequence, pp. 19–33 (1995).

*Primary Examiner*—Diego Gutierrez
*Assistant Examiner*—Dixomara Vargas
(74) *Attorney, Agent, or Firm*—Kevin P. McEnaney; Brigitte L. Jeffery; John H. Ryberg

(57) ABSTRACT

One embodiment of the present invention is a method for nuclear magnetic resonance imaging of an investigation region of formation surrounding a wellbore. The method comprises the steps of applying a series of magnetic field gradients to phase encode nuclear spins within the investigation region, wherein the strength of the magnetic field gradient applied is different from at least one previously applied magnetic field gradient within the series. Nuclear magnetic resonance signals are detected from the investigation region resulting from the series of magnetic field gradients.

73 Claims, 14 Drawing Sheets

U.S. PATENT DOCUMENTS

| | | |
|---|---|---|
| 6,255,817 B1 | 7/2001 | Poitzsch et al. ............ 324/303 |
| 6,268,726 B1 | 7/2001 | Prammer et al. ........... 324/303 |
| 6,291,995 B1 | 9/2001 | Speier et al. |
| 6,297,632 B1 | 10/2001 | Speier |
| 6,326,784 B1 * | 12/2001 | Ganesan et al. ............ 324/303 |
| 6,342,784 B1 * | 1/2002 | Wollin ........................ 324/303 |
| 6,366,089 B1 | 4/2002 | Poitzsch et al. |
| 6,373,248 B1 | 4/2002 | Poitzsch et al. |
| 6,392,410 B2 | 5/2002 | Luong et al. |
| 6,400,149 B1 | 6/2002 | Luong et al. |
| 6,492,809 B1 | 12/2002 | Speier et al. |
| 6,518,757 B1 | 2/2003 | Speier |
| 6,518,758 B1 | 2/2003 | Speier et al. |
| 6,522,136 B1 * | 2/2003 | Hurlimann et al. ......... 324/303 |
| 6,522,137 B1 * | 2/2003 | Sun et al. ................... 324/303 |
| 6,528,995 B1 | 3/2003 | Speier et al. |
| 6,531,869 B1 | 3/2003 | Speier et al. |
| 6,538,438 B1 | 3/2003 | Speier et al. |
| 6,566,874 B1 | 5/2003 | Speier et al. |
| 6,570,381 B1 | 5/2003 | Speier et al. |

* cited by examiner

NUCLEAR MAGNETIC RESONANCE IMAGING USING PHASE ENCODING WITH NON-LINEAR GRADIENT FIELDS

BACKGROUND OF THE INVENTION

1. Field of the Invention

This invention relates to the field of wellbore logging and, more particularly, to a method and apparatus for determining nuclear magnetic resonance logging characteristics of earth formations surrounding a wellbore, as a function of angular position about the borehole, either during the drilling of the wellbore or after drilling.

2. Description of Related Art

Hydrocarbon fluids, such as oil and natural gas, are obtained from a subterranean geologic formation, referred to as a reservoir, by drilling a wellbore that penetrates the hydrocarbon-bearing formation. An understanding of the reservoir physical properties, often referred to as formation evaluation, is needed to determine the well's productive capacity, recoverable reserves, size and type of production equipment needed, and many other issues relating to the well's drilling, completion and production. Specific reservoir properties that are desired include, for example, porosity, permeability, and water saturations.

Electrical "logging" dates back to 1912, when Conrad Schlumberger began studying the problem of exploring the underground by means of surface electrical measurements. Since that time, various types of well logging techniques have been developed, such as acoustic, temperature, resistivity, nuclear, and gamma-ray measurement techniques.

Nuclear magnetic resonance (NMR) imaging involves the physical principle that various nuclei will precess at different frequencies in an imposed magnetic field. Many nuclei have a magnetic moment and behave much like a spinning bar magnet. This spinning motion is often referred to in the NMR terminology as the particle spin and is illustrated in FIG. 27. Hydrogen nuclei, consisting of a single proton, has a relatively large magnetic moment and is found in both water and hydrocarbons that are located within a reservoir matrix. An externally applied magnetic field can interact with the spinning hydrogen protons and can produce measurable effects. An NMR logging tool can be designed to operate at the magnetic resonant frequency of hydrogen, thereby allowing the tool to alter and detect the responses of the hydrogen protons within the region of investigation. By altering and detecting responses, the tool can obtain information relating to the water and hydrocarbons within the reservoir.

A static magnetic field is generated by the tool to initially align the hydrogen protons in the formation fluids. An oscillating radio-frequency magnetic field is generated by the tool to alter the hydrogen protons alignment and tip the protons in a transverse plane. The tipped protons move in a precessional motion around the initial alignment position in a manner similar to a spinning top that precesses in the Earth's magnetic field, as illustrated in FIG. 27. Various NMR measurements of these and other related effects can provide an indication of the amount of total fluid contained within the formation, and can be used to indicate the identity of the fluid, whether water, gas or oil. The measurements can also provide indications on the pore and grain size distribution of the formation matrix and whether the fluids are bound within the formation matrix or are capable of movement, and therefore, potentially producible.

One approach to obtaining nuclear magnetic resonance measurements involves inserting a NMR tool within the wellbore and applying a locally generated static magnetic field $B_o$, which can be produced by one or more electromagnets or permanent magnets. The spins of the hydrogen protons within the formation matrix near the tool are aligned with the applied field Bo, generating a net nuclear magnetization as the spinning hydrogen protons precess about the imposed magnetic field $B_o$, as illustrated in FIG. 28. Nuclear spins of the hydrogen protons align with the applied field $B_o$, generating a net nuclear magnetization. Applying an RF field, $B_1$, perpendicular to the static field $B_o$, as illustrated in FIG. 29, can change the angle between the nuclear magnetization and the applied field $B_o$. The frequency of the RF field should be equal to the Larmor frequency given by $\omega_0 = \gamma B_o$ where $\gamma$ is the gyromagnetic ratio. After application of an RF pulse, the magnetization begins to precess around $B_o$ and produces a detectable signal in the antenna. As the protons precess about the static field $B_o$, they gradually lose synchronization with each other, as illustrated in FIG. 30. This loss of synchronization causes the magnetic field in the transverse plane to decay. Phase encoding is caused by inhomogeneities in the static magnetic field and by molecular interactions. The signals can be analyzed to detect nuclear magnetic resonance properties of the formation and provide information relating to porosity, free fluid ratio, permeability, and other properties of the formation. See U.S. Pat. No. 4,717,878 issued to Taicher et al. and U.S. Pat. No. 5,055,787 issued to Kleinberg et al.

Another approach to obtaining nuclear magnetic resonance measurements employs a locally generated static magnetic field, $B_o$, which may be produced by one or more permanent magnets or electromagnets, and an azimuthally-oriented oscillating magnetic field, $B_1$, which may be produced by one or more RF antenna segments that transmit and/or receive from different circumferential sectors of the logging device. See U.S. Pat. Nos. 5,977,768 and 6,255,817 assigned to Schlumberger Technology Corporation.

U.S. Pat. No. 5,796,252 issued to Kleinberg et al. describes a nuclear magnetic logging device that includes permanent magnets, an RF antenna, and a coil for generating a magnetic field gradient. The technique described in the '252 patent utilizes pulsed magnetic field gradients to obtain information regarding diffusion properties of the formation fluids. If internal gradients are present in the formation, a pulse sequence is applied to reduce or substantially eliminate the effect of internal gradients in the formation. The '252 patent does not identify a method for using the coil to obtain an azimuthal NMR measurement.

U.S. Pat. No. 5,212,447 issued to Zvi Paltiel describes a nuclear magnetic logging device that includes permanent magnets and an RF antenna coil. The '447 patent requires a magnetic field gradient coil to determine a diffusion coefficient, i.e., the rate at which molecules of a material randomly travel within the bulk of the same material. The '447 patent employs the diffusion coefficient to determine at least one of the following petrophysical parameters: water/hydrocarbon discrimination, water and hydrocarbon saturation levels, permeability, pore size and pore size distribution, oil viscosity, a measure of the average increase in electrical resistance due to the formation tortuosity, and q-space imaging of the formation. The '447 patent does not identify a method for using the coil to obtain an azimuthal NMR measurement.

U.S. Pat. No. 6,326,784 assigned to Schlumberger Technology Corporation, discloses a means to obtain azimuthal NMR measurements using one or more gradient coils and an axi-symmetric antenna. In this approach, a pulse sequence and a firing of a gradient coil is used in conjunction to obtain an azimuthal image. The resolution of the azimuthal image depends on the number of gradient coils used and the angular coverage of each gradient coil. The gradient coils are positioned circumferentially and are separated by an angular distance, for example, three gradient coils located around an NMR tool spaced 120° from each other. Each gradient coil is used to spoil or rotate the hydrogen proton spins within the formation matrix adjacent to the gradient coil, with negligent effects everywhere else. The NMR data obtained after the pulse sequence and firing of a gradient coil is used to obtain formation evaluation information of the reservoir adjacent to the gradient coil. This process is repeated for the other gradient coils to obtain the azimuthal image.

One method for acquiring azimuthal data is the binning of the measured data. In this acquisition scheme, a plurality of azimuthal bins is defined and each NMR measurement is added to the content of a buffer associated with the bin in which the measurement was taken. To obtain a good statistical quantity of data for each bin and to ensure that in each bin there are enough measurements, this scheme requires numerous individual measurements. For example, for one particular embodiment having a 90° resolution, seven bins are preferable, with ten measurements per bin, or 70 measurements per scan. Better resolution, (i.e., smaller angular distances between gradient coils), would need substantially more measurements and result in substantially more time required to obtain the quantity of data needed.

There is a need for improved means to obtain NMR azimuthal images of a formation. There is also a need for greater azimuthal resolution of the formation properties, along with means to obtain this information with less acquisition time.

SUMMARY OF THE INVENTION

One embodiment of the present invention is a method for nuclear magnetic resonance imaging of an investigation region of formation surrounding a wellbore. The method comprises the steps of applying a series of magnetic field gradients to phase encode nuclei spins within the investigation region, wherein the strength of the magnetic field gradient applied for each spin-echo signal is different from at least one previously applied magnetic field gradients within the series. Nuclear magnetic resonance signals are detected from the investigation region resulting from the series of magnetic field gradients.

Another embodiment of the invention is an apparatus for determining a nuclear magnetic resonance property in an investigation region of earth formations surrounding a wellbore. The apparatus comprises a logging device moveable through the wellbore and a means in the logging device for applying a static magnetic field circumferentially around the wellbore and into the investigation region. The apparatus further comprises an antenna means in the logging device for applying an RF magnetic field circumferentially around the borehole and into the investigation region, whereby the antenna means induces a plurality of pulse echoes and spin-echo signals from selected nuclei of the formation. A gradient means in the logging device is capable of producing a gradient magnetic field circumferentially around the borehole and into the investigation region and is capable of producing different strength gradient magnetic fields for each of the plurality of pulse echoes, wherein the orientation of the gradient magnetic field and the static magnetic field effects on the selected nuclei vary depending on the azimuthal position around the wellbore in relation to the gradient means and means for detecting nuclear magnetic resonance signals from the investigation region.

BRIEF DESCRIPTION OF THE DRAWINGS

The invention may be understood by reference to the following description taken in conjunction with the accompanying drawings, in which like reference numerals identify like elements, and in which.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
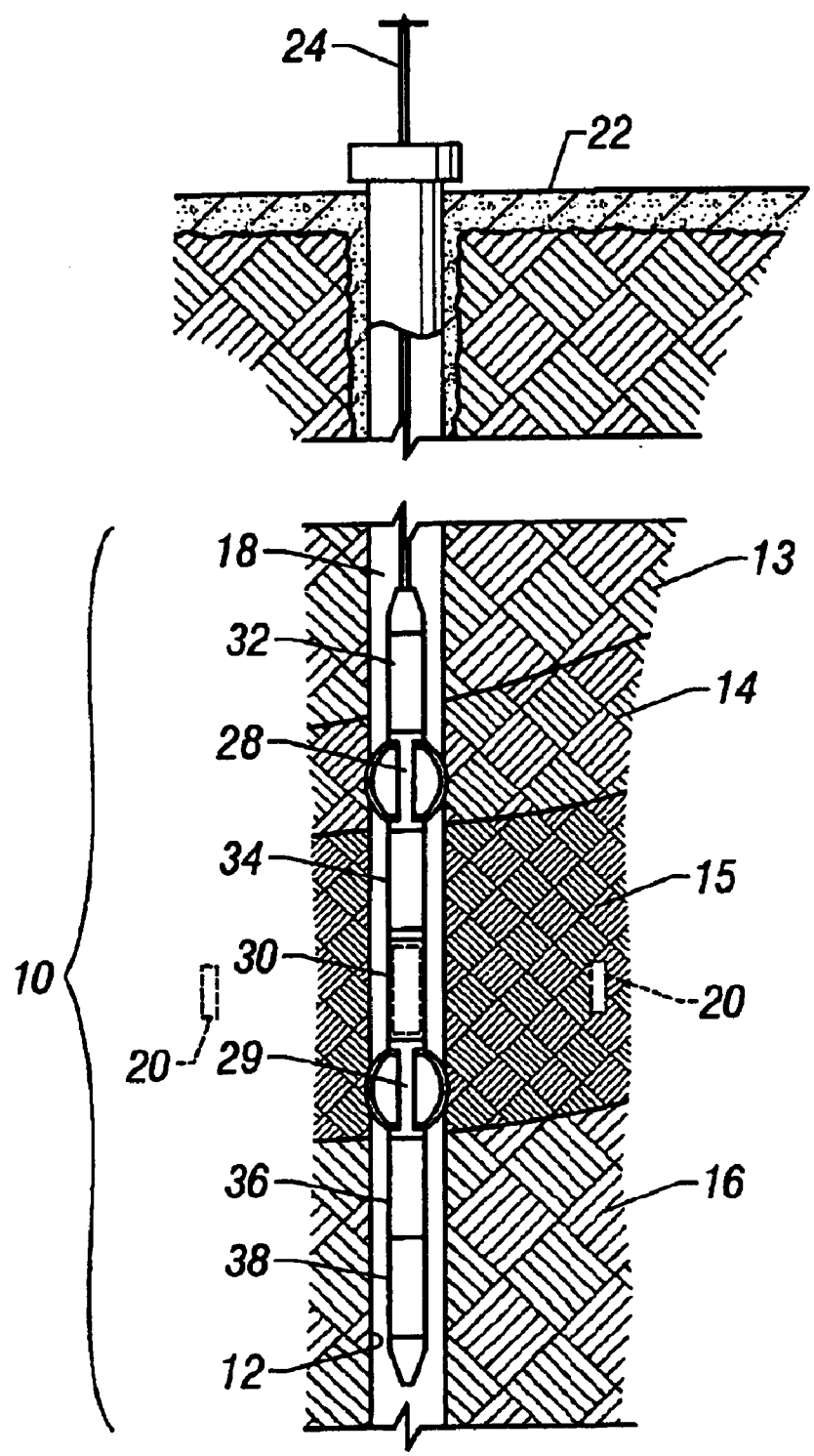
FIG. 1 shows a well logging apparatus in which embodiments of the invention can be practiced.

FIG. 1 shows a well logging apparatus 10 in which embodiments of the invention can be practiced. The well logging apparatus 10 is disposed in a wellbore 12 drilled from the surface 22 and it is capable of making measurements of properties of the various earth formations 13, 14, 15, 16. The wellbore 12 is typically filled with a liquid 18 such as drilling mud or completion fluids. A region within a particular formation 15 exposed to nuclear magnetic resonance ("NMR") imaging is shown generally as 20 and it has a generally cylindrical shape extending within the formation and proceeding around the wellbore. The well logging apparatus 10, which can include an NMR tool 30, can be lowered into the wellbore 12 by means of a wireline 24 that can provide electrical power and transmit signals to the surface 22. Surface equipment (not shown) can include a telemetry system for communicating with the tool string, recording instruments, computers, and the like. The well logging apparatus 10 is often centered within the wellbore 12 by means of a top centralizer 28 and a bottom centralizer 29 attached to the well logging apparatus 10 at axially spaced locations. The centralizers 28, 29 can be of various types known in the art, such as bowsprings.

Other well logging sensors may form part of the well logging apparatus 10. Additional logging sensors 32, 34 may be located above the NMR probe 30 while other logging sensors, 36, 38 may be located below the NMR probe 30. The other sensors 32, 34, 36, 38, can be of types familiar to those skilled in the art and can include, but are not limited to, pressure and temperature sensors, gamma ray detectors, formation bulk density sensors or neutron porosity detectors. The locations of the other sensors 32, 34, 36, 38 are a matter of convenience and are not to be construed as a limitation on the invention.

Figure 2:
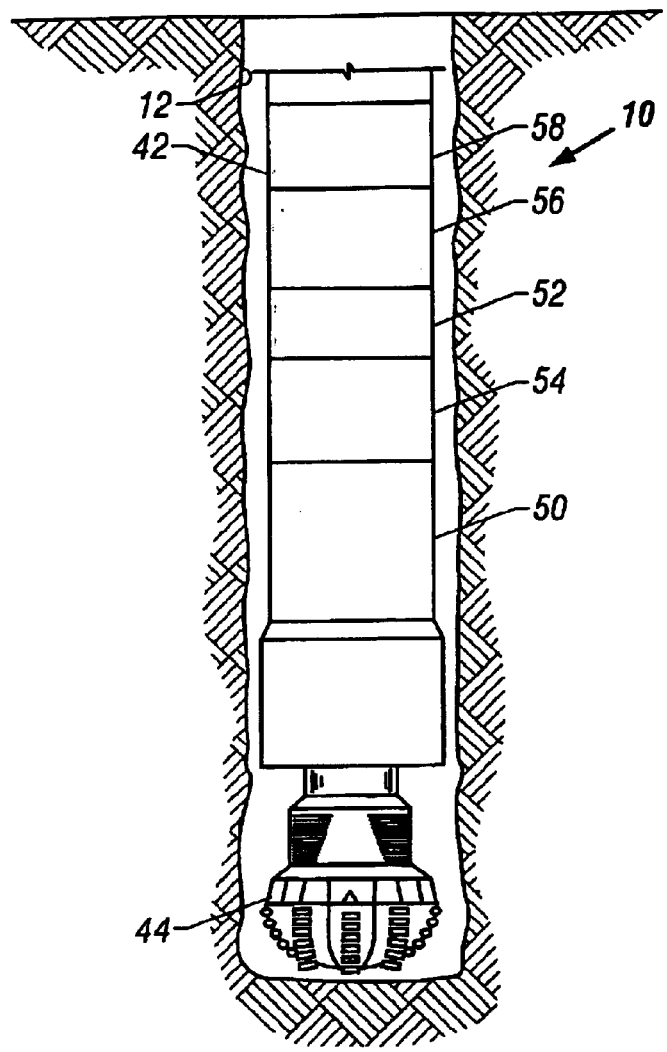
FIG. 2 illustrates a logging while drilling (LWD) apparatus in which embodiments of the invention can be practiced.

Referring to FIG. 2, there is illustrated a logging while drilling (LWD) apparatus 40 in which embodiments of the invention can be practiced. A drill string 42 is disposed within the wellbore 12 and includes a drill bit 44 at its lower end. The drill string 42, and the drill bit 44 can be rotated by a rotating table (not shown) that engages a kelly (not shown) at the upper end of the drill string 42. Alternatively, the drill string 42 may be rotated from the surface by a "top drive" type of drilling rig. Alternatively, the drill string 42 may comprise a downhole motor (not shown) that rotates the drill bit 44, without requiring the rotation of the drill string 42. Drilling fluid, often referred to as mud, is pumped downward through a channel in the center of drill string 42. The drilling fluid exits the drill string 42 via ports in the drill bit 44 and then circulates upward in the region between the outside of the drill string 42 and the periphery of the wellbore 12. The drilling fluid thereby carries formation cuttings to the surface of the earth.

Tools designed for logging while drilling 50 (LWD), measurement while drilling 52 (MWD), or a combination of both (LWD/MWD) can be connected to the drill string 42. A typical MWD tool 52 measures and/or computes the direction, inclination, and rotational orientation of the bottom hole assembly. An MWD tool useful with the subject invention is described, for example, in U.S. Pat. No. 5,473,158. The driving electronics module 54 and acquisition and processor electronics module 56 are coupled to and obtain measurement information from the LWD tool 50.

Figure 3:
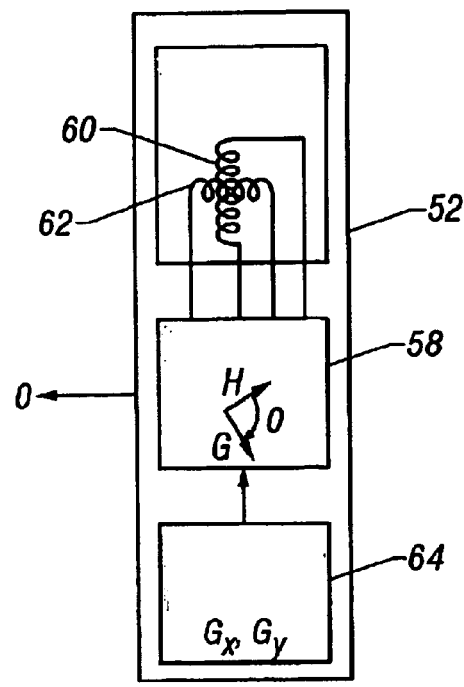
FIG. 3 illustrates a MWD tool that includes magnetometers $H_x$ and $H_y$ oriented along x and y axes of the tool that can include embodiments of the present invention.

FIG. 3 illustrates a MWD tool 52 that includes magnetometers $H_x$ and $H_y$ (60, 62) oriented along x and y axes of the tool that can include or be used in conjunction with embodiments of the present invention. The MWD tool 52 can be used to gather alignment information relating the orientation of the present invention with surface orientations, such as the directional orientation of formation properties (e.g., a north-east by south-west aligned fractured zone through the formation). Such x and y axes are in the plane of a radial cross section of the tool. A z-axis of the tool is oriented along its longitudinal axis. In a similar way, accelerometers $G_x$ and $G_y$ of the accelerometer package 64 (which also includes an accelerometer along the z-axis of the tool) are oriented along the x and y axes of the tool. A microcomputer 58 responds to $H_x$ and $H_y$ signals and $G_x$ and $G_y$ signals to constantly determine an angle φ between an $\vec{H}'$ vector and the $\vec{G}'$ vector, in the cross sectional plane of the MWD tool 52. The $\vec{H}'$ vector represents that portion of a vector pointed to earth's magnetic north pole that is projected onto the x-y plane of MWD tool 52. The $\vec{G}'$ vector represents the down component in the cross sectional plane of tool 52 of the earth's gravity vector. A signal representative of such angle φ is constantly communicated to the downhole computer 58 (which includes a Quadrant/Coil Position Determination program). The MWD tool 52 can be used in conjunction with the present invention to distinguish the azimuthal location and orientation of angular segments of the formation around the wellbore. Various embodiments of this type of MWD tool can be utilized in rotational drilling operations, in non-rotational drilling operations in which the drill string moves primarily longitudinally through the wellbore, and also in wireline conveyed logging applications.

Figure 4:
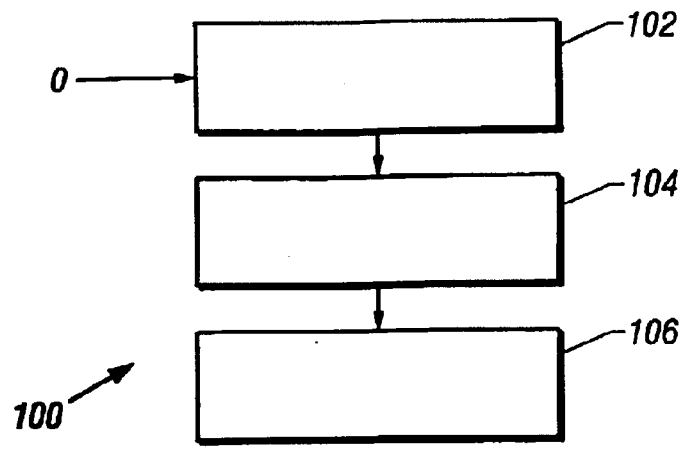
FIG. 4 is a flow chart that describes the Quadrant/Coil Position Determination Program.

FIG. 4 is a flow chart that describes the Quadrant/Coil Position Determination Program 100. As explained above, an angle $\phi$ is constantly computed between the $\vec{H}'$ vector (a constantly directed vector in the x-y plane for a vector directed to earth's magnetic pole) and a $\vec{G}'$ vector (a constantly directed down vector in the x-y plane of a vector directed to the earth's gravitational center). As the tool rotates in the wellbore, the x and y axes of the device rotate at the angular speed of the drill string so the x and y components of the $\vec{H}'$ vector and $\vec{G}'$ vector are constantly changing with time. Further, as the device rotates in the wellbore, an angle $\theta(t)$ is constantly formed between the tool x-axis and such $\vec{H}'$ vector. The angle $\theta(t)$ is determined from the $H_x$ and $H_y$ signals from magnetometers 60 and 62 and the angle varies with time because it is measured from the x-axis of the MWD tool 42 (and the LWD tool 50) to the $\vec{H}'$ vector.

At step 102, the down vector angle, $\angle\vec{D}(t)$, is determined in Quadrant/Coil Position Determination program 100, according to the following relationship, as a function of the x and y axes and time:

$$\theta(t) = \cos^{-1}\left[\frac{H_x(t)}{\sqrt{(H_x(t)^2 + H_y(t)^2)}}\right].$$

The angle of the down vector is determined in the program as $\angle\vec{D}(t)=\theta(t)-\phi$.

At step 104, four quadrants may be defined by angular ranges about the periphery of the tool:

$Q_{BOT}(t)=\angle\vec{D}(t)-45°$ to $\angle\vec{D}(t)+45°$ $Q_{LEFT}(t)=\angle\vec{D}(t)+45°$ to $\angle\vec{D}(t)+135°$ $Q_{TOP}(t)=\angle\vec{D}(t)+135°$ to $\angle\vec{D}(t)+225°$ $Q_{RIGHT}(t)=\angle\vec{D}(t)+225°$ to $\angle\vec{D}(t)-45°$.

The term "quadrant" is used to illustrate the invention where four 90° angular distance segments are defined around the 360° circumference of the MWD device or the LWD tool. Other angular distance segments, sometimes referred to as zones or segments, may be defined having resolutions other than 90°. The smaller the angle of investigation, the greater the formation resolution is obtained.

Figure 5:
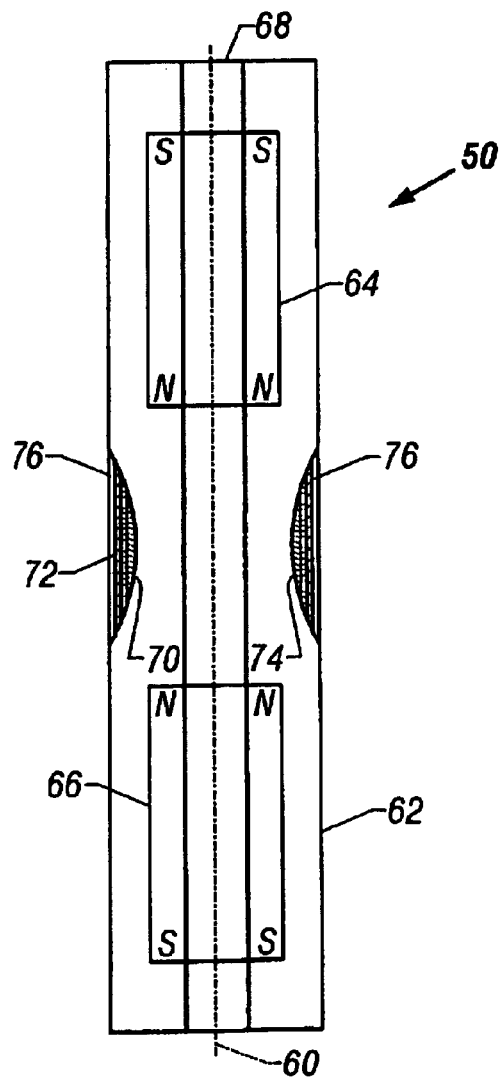
FIG. 5 illustrates a nuclear magnetic resonance (NMR) logging-while-drilling tool in accordance with one embodiment of the invention.

FIG. 5 illustrates a nuclear magnetic resonance (NMR) logging-while-drilling tool 50 in accordance with one embodiment of the invention. The tool 50 has an axis 60 and can comprise a portion of a drill collar 62, which is substantially aligned with the axis of the wellbore. A static magnetic field is produced by tubular, axially polarized, permanent magnets 64, 66 that are mounted inside the drill collar 62. A channel 68 located inside the tool permits drilling mud to flow toward the drill bit. In the region between the magnets 64, 66, there is a recessed area 70. An RF antenna 72 is provided in the recessed area 70, which can be used for detecting NMR signals. However, a separate antenna or receiver may be used to detect the signals. A non-conductive material 74 can be provided in the recessed area 70 beneath the antenna 72. The material 74 may be a ferrite to increase the efficiency of the antenna 72. Alternatively, the material 74 may comprise a plastic, rubber, or a reinforced epoxy composite material.

Figure 9:
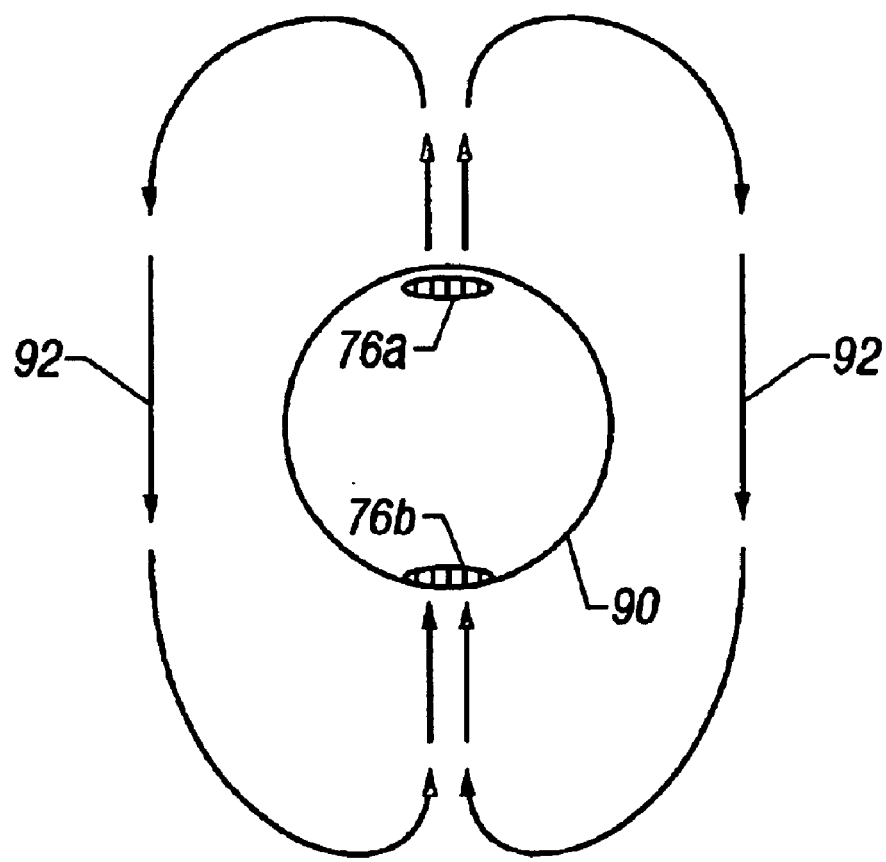
FIG. 9 illustrates a cross sectional view of an embodiment of a nuclear magnetic resonance (NMR) tool and an induced magnetic field imposed to the gradient coil, in accordance with one embodiment of the invention.

Still referring to FIG. 5, in order to obtain azimuthal NMR measurements, at least one gradient coil 76 can be arranged in the recessed area 70. The geometry of the gradient coil 76 (e.g., a saddle coil) can produce a magnetic field around the tool 50, as illustrated in FIG. 9. The gradient magnetic field will add to or subtract from the static magnetic field, depending on its azimuthal orientation to the gradient coil. It should be noted that the method and gradient coils of the subject invention can also be used with any tool that generates a rotationally symmetric static magnetic field, for example, the tools disclosed in U.S. Pat. No. 5,757,186 issued to Taicher et al., and U.S. Pat. No. 5,280,243 issued to Melvin Miller.

Figure 6:
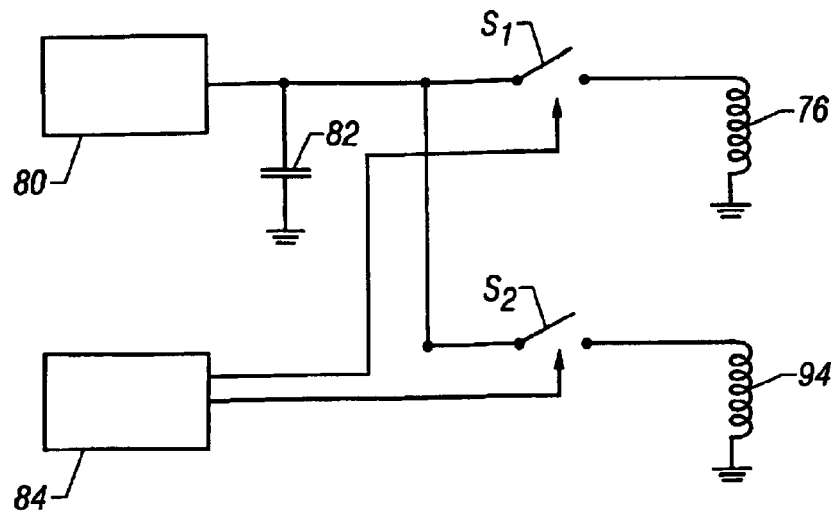
FIG. 6 is a diagram of the firing circuitry for use in conjunction with an embodiment of the invention having two gradient coils.
Figure 14:
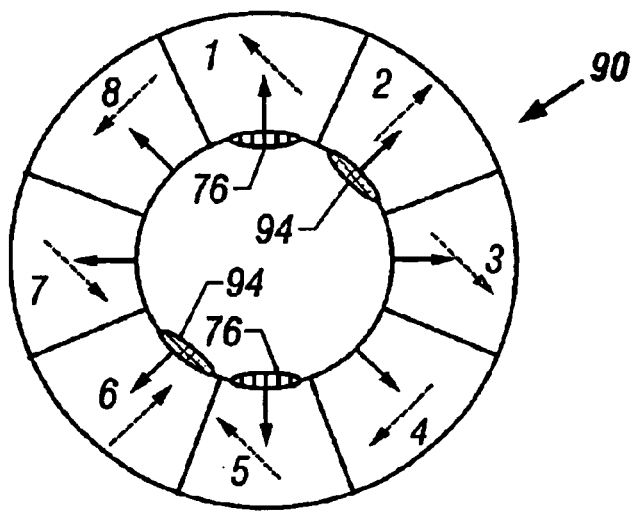
FIG. 14 illustrates a cross sectional view of an embodiment of a nuclear magnetic resonance (NMR) tool, in accordance with one embodiment of the invention.

FIG. 6 is a diagram of an embodiment of the circuitry included in the driving electronics module 54 for use in conjunction with an embodiment having two gradient coils 76 and 94. An example of a tool having two gradient coils is illustrated in FIG. 14. The driving electronics include a high voltage power supply 80 and capacitor 82. Switches $S_1$ and $S_2$ are under the control of timing control/coil selection hardware 84. The gradient coils 76 and 94 are coupled, via the switches, to the timing control/coil selection hardware 84. The pulse sequence created by the gradient coils can also comprise applying a fixed or variable wait time between the gradient pulse and the RF pulse.

Figure 7:
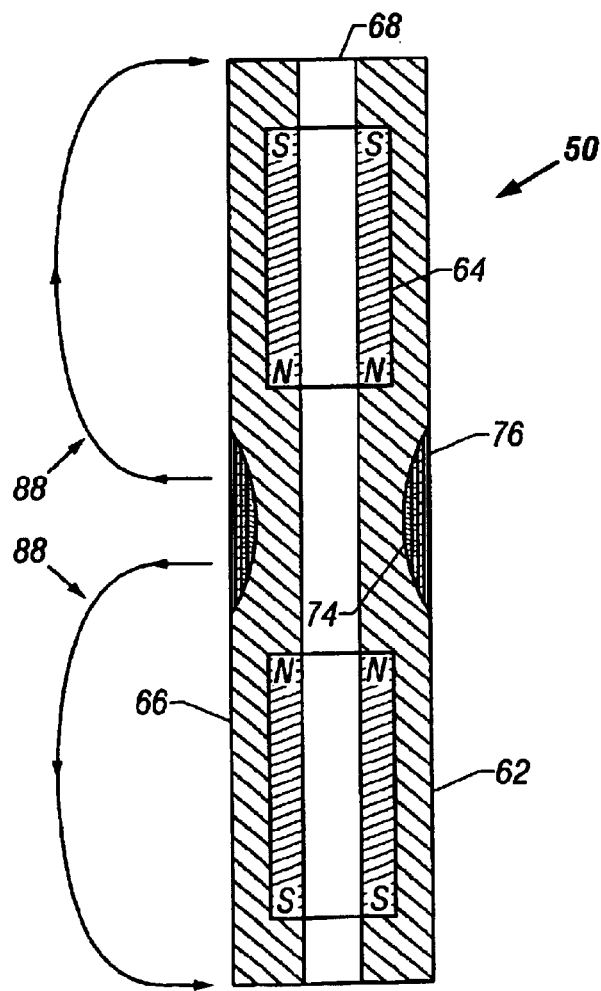
FIG. 7 illustrates a nuclear magnetic resonance (NMR) logging-while-drilling tool in accordance with one embodiment of the invention.

FIG. 7 illustrates a nuclear magnetic resonance (NMR) logging-while-drilling tool 50 in accordance with one embodiment of the invention. A static magnetic field 88 is produced by tubular, axially polarized, permanent magnets 64, 66 that are mounted inside the drill collar 62. The static magnetic field 88 generated by the magnets 64, 66 extends out radially from the tool 50 into the formation that is axially adjacent to the gradient coil 76. The static magnetic field 88 can also be developed using an electrical current flowing through coils within the tool 50.

Figure 8:
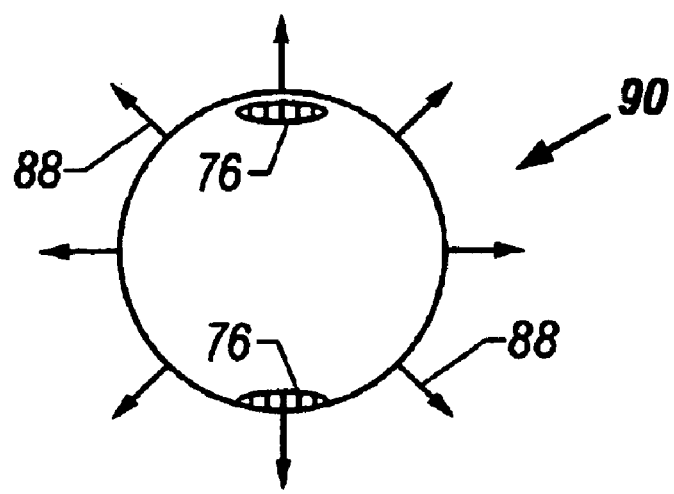
FIG. 8 illustrates a cross sectional view of a nuclear magnetic resonance (NMR) tool having the induced static magnetic field adjacent to the gradient coil, in accordance with one embodiment of the invention.

FIG. 8 illustrates a cross sectional view of a nuclear magnetic resonance (NMR) tool 90 having the induced static magnetic field 88. The induced static magnetic field 88 extends out radially into the formation that is axially adjacent to the gradient coil 76.

FIG. 9 illustrates a cross sectional view of an embodiment of a nuclear magnetic resonance (NMR) tool 90 wherein the geometry of the gradient coil (e.g., saddle coil) 76 is such that it produces a polarized magnetic field 92 around the tool 90. The magnetic field 92 extends from one end of the gradient coil 76a, proceeds circumferentially through the adjacent formations on either side of the tool 90, and returns to the other end of the gradient coil 76b. The gradient magnetic field 92 is oriented circumferentially into the investigation region relative to the wellbore.

Figure 10:
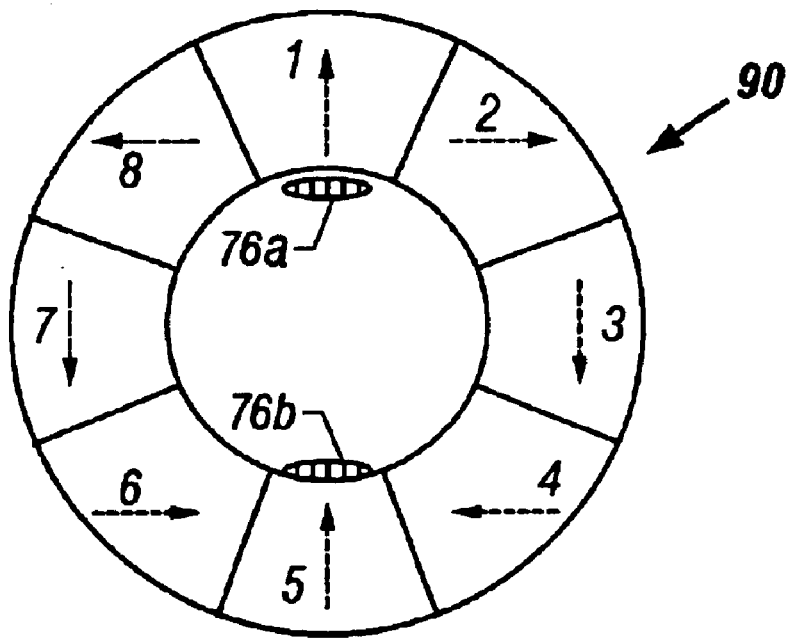
FIG. 10 illustrates a cross sectional view of an embodiment of a nuclear magnetic resonance (NMR) tool and an induced magnetic field imposed to the gradient coil shown as an approximate average for each segment of the investigation region, in accordance with one embodiment of the invention.

FIG. 10 illustrates a cross sectional view of an embodiment of a nuclear magnetic resonance (NMR) tool 90 wherein the geometry of the gradient coil 76 produces a magnetic field 92 around the tool. The formation around the tool is shown divided into eight zones, each zone representing an azimuthal angle of 45°. The dashed arrows show an approximation of the average orientation of the gradient coil magnetic field 92 within each zone. The magnetic field 92 extends from one end of the gradient coil 76a, proceeds through the adjacent formations on either side of the tool 90, and returns to the other end of the gradient coil 76b. The gradient magnetic field 92 exerts differing directional magnetic forces, depending on its azimuthal position relative to the gradient coil 76 for each zone. The gradient magnetic field amplitude is not linear, but varies relative to the cosine of the azimuthal angle from the gradient coil, therefore the dashed arrows should not be interpreted to indicate the actual direction and strength or the magnetic field 92, but only a generalized indication.

Figure 11:
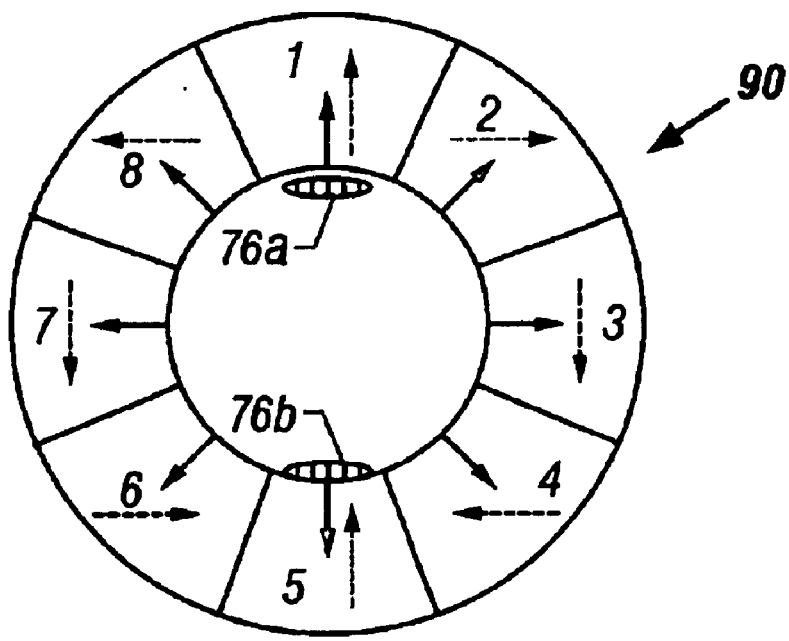
FIG. 11 illustrates a cross sectional view of an embodiment of a nuclear magnetic resonance (NMR) tool and an induced magnetic field imposed to the gradient coil shown as an approximate average for each segment of the investigation region along with the induced static magnetic field, in accordance with one embodiment of the invention.

FIG. 11 illustrates a cross sectional view of an embodiment of a nuclear magnetic resonance (NMR) tool 90 wherein the geometry of the gradient coil 76 produces a magnetic field 92 around the tool. The formation around the tool is shown divided into eight zones, each zone representing an azimuthal angle of 45°. The dashed arrows show an approximate average of the magnetic field orientation of the gradient coil magnetic field 92 on each zone. The magnetic field 92 extends from one end of the gradient coil 76a, proceeds through the adjacent formations on either side of the tool 90, and returns to the other end of the gradient coil 76b. The gradient magnetic field amplitude is not linear, but varies relative to the cosine of the azimuthal angle from the gradient coil, therefore the dashed arrows should not be interpreted to indicate the actual direction and strength or the magnetic field 92, but only a generalized indication. The solid arrows show the static magnetic field 88. The gradient coil field 92 acts to increase the static magnetic field 88 by a maximum amount in zone 1, decrease the static magnetic field 88 by a maximum amount in zone 5, and have effects between these two extremes in the other zones. The eight zones are typically fixed in space relative to the gradient coil 76, but can be defined as a function of time if the tool is rotating, as in some embodiments of a logging while drilling (LWD) application, (see prior discussion involving FIGS. 3 and 4).

In the typical NMR measurement application, a pulse sequence is applied to the formation under investigation. In one embodiment of the invention a pulse sequence, such as the Carr-Purcell-Meiboom-Gill (CPMG) sequence, first applies an excitation pulse, a 90° pulse, to the formation that rotates the spins into the transverse plane (relative to the static magnetic field). After the spins are rotated by 90° and start to dephase, the carrier of the refocusing pulses, the 180° pulses, is phase shifted relative to the carrier of the 90° pulse sequence according to the following relationship:

$$t_{90°_{\pm x}} - t_0 - [t_{180°_y} - t_1 - \text{echo}_{max}^n - t_2]_n,$$

where the bracketed expression is repeated for n=1, 2, ... N, where N is the number of echoes collected in a single CPMG sequence and the echo spacing is $t_{echo} = 2t_{cp} = t_{180°_y} + t_1 + t_2$. The term $90°_{\pm x}$ denotes an RF pulse that causes the spins to rotate by a 90° angle about the ±x-axis, as commonly defined in the rotating frame of magnetic resonance measurements (phase alternated). The time between application of the 90° pulse and the 180° pulse, $t_0$, is less than $t_{cp}$, half the echo spacing. The CPMG sequence enables acquisition of a symmetric measurement (i.e., a measurement without using the gradient coils). The exact timing parameters, $t_0$, $t_1$, and $t_2$, depend on various factors (e.g., the shape of the applied pulses).

Figure 12:
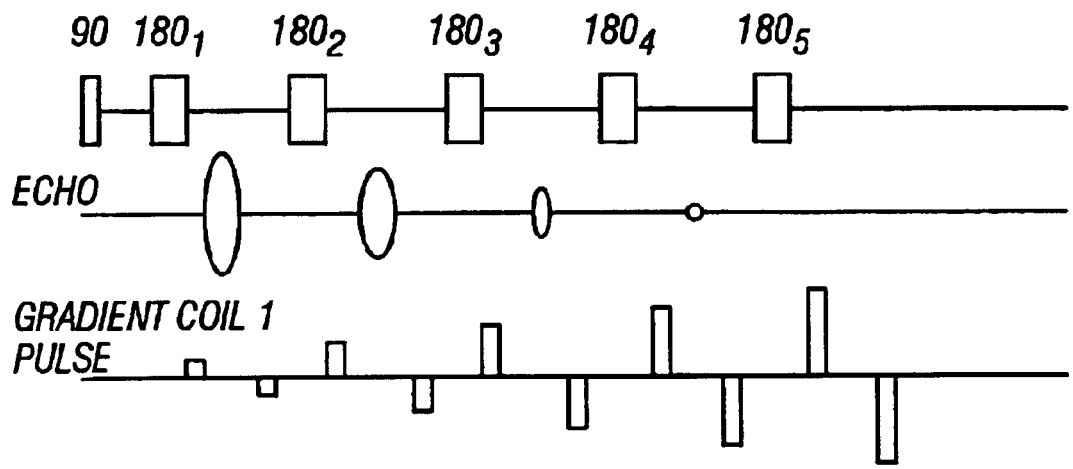
FIG. 12 illustrates the pulse sequence used to obtain the azimuthal resolution imaging for one embodiment of the present invention.

FIG. 12 illustrates the pulse sequence used to obtain the azimuthal resolution imaging for one embodiment of the present invention. Referring to FIGS. 8–11, a current pulse applied to the gradient coil 76 generates an additional magnetic field 92, altering the static magnetic field 88 within the formation matrix, depending on its position relative to the gradient coil 76. The gradient coil current amplitude is different for each consecutive echo in the CPMG pulse sequence, so that at each consecutive echo, the nuclear spin alignments within the formation matrix are rotated by a different angle. Within the present application the phrases of "different gradient current amplitude" or "altering the gradient amplitude" and the like can include incrementing, decrementing or other means of altering the amplitude such that it is not the same amplitude as at least one previous gradient coil pulses, thus imparting distinct pulse amplitudes on some or all of the altered echoes. The currents shown in the figures illustrate increasing current amplitudes, but other patterns of alteration can also be used. The amplitude of the gradient pulse that provides the greatest phase change has to be at least strong enough to impose an altered phase difference between adjacent formation segments (areas of investigation or resolution) of at least 180 degrees, thereby completely dephasing neighboring formation segments.

Typically the gradient coil current amplitude is altered for each consecutive echo, but keeping consistent gradient coil current amplitudes and increasing the incremental times between the pulses can obtain a similar effect. Generally shorter, more consistent time periods are preferred within the pulse sequence; therefore the current amplitude is generally the variable that is altered. The gradient coil current pulse is applied just before each echo. The gradient coil current is then reversed at the same amplitude after each echo so that phase encoding or rotational effects due to the gradient pulse are cancelled before the next 180° phase reversing pulse.

Since the strength of the static magnetic field 88 is much greater than the gradient coil magnetic field 92, the only component of the gradient coil magnetic field 92 that has an effect on the nucleus spins is those components that are parallel or anti-parallel to the static magnetic field 88. Only the component of the gradient field 92 along the static magnetic field 88 orientation is responsible for the changes in the precession frequency (or phase) of the spins, i.e. that portion of the gradient coil magnetic field 92 that is parallel or anti-parallel in respect to the static magnetic field 88.

For the embodiment of the invention using the pulse sequence as shown in FIG. 12, the gradient coil pulse is applied to the five echoes in the CPMG sequence. The echo amplitude with respect to the gradient pulse amplitude is analyzed using Fourier transforms, which results in data that can be grouped within five bins representing NMR signal intensities. The NMR signal intensities from the various bins correspond to either individual zones or combinations of the zones of the formation located around the NMR tool. U.S. Pat. No. 6,326,784 assigned to Schlumberger Technology Corporation discloses one means of utilizing Fourier transforms of NMR signals that can be grouped within bins, the binned data representing groupings of NMR signals obtained from one or more azimuthal zones around the NMR tool.

Figure 13:
FIG. 13 is a table showing the NMR signals from various zones arranged in five bins, in accordance with one embodiment of the invention.

FIG. 13 is a table showing how the NMR signal intensities from the five bins corresponding to zone 1, zones 2 and 8, zones 3 and 7, zones 4 and 6, and zone 5, respectively. Zones 1 and 5 can be individually distinguished since they each are in a bin by themselves, however the other six zones are in combinations within the bins and therefore cannot be directly distinguished. Since the gradient magnetic field amplitude is not linear, but varies relative to the cosine of the azimuthal angle from the gradient coil, the zones 1 through 8 will comprise differing azimuthal angles and will therefore provide data for differing angular segments of the formation. At this stage of the formation evaluation, the opposing zones 1 and 5, alternately referred to as top and bottom segments, can be quantified and are obtained using a single gradient coil. The time to obtain this data is the time required to generate and detect five CPMG echoes. To quantify other formation segments, in one embodiment of the invention, the NMR tool can be rotationally adjusted to a new azimuthal position, and the method described above repeated.

FIG. 14 illustrates a cross sectional view of an embodiment of a nuclear magnetic resonance (NMR) tool 90 where a second gradient coil 94 is oriented at 45 degrees (e.g. facing hypothetical zones 2 and 6) from the original gradient coil 76. The dashed arrows illustrate an approximate orientation of the magnetic field generated by the second gradient coil 94 on each zone. The solid arrows represent the static magnetic field 88. The various segments of the formation matrix are typically fixed in space relative to the gradient coil 94, but can be defined as a function of time if the tool is rotating, as in some embodiments of a LWD application. The CPMG sequence as shown in FIG. 12 can be repeated for the second gradient coil 94, or the second gradient coil firing can be performed within the same pulse sequence after the first gradient coil firing.

Figure 15:
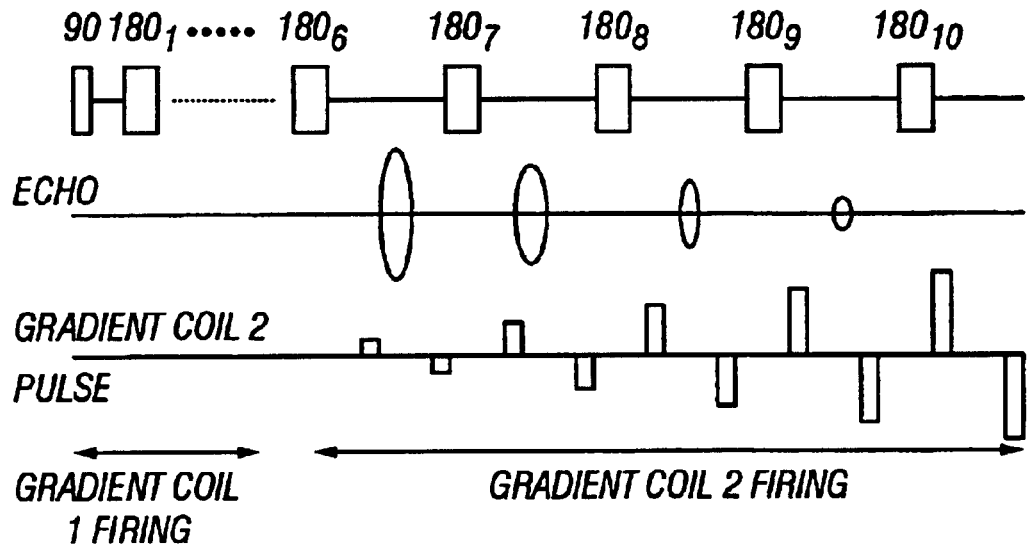
FIG. 15 illustrates the pulse sequence used to obtain the azimuthal resolution imaging for an alternative embodiment of the present invention.

FIG. 15 illustrates the pulse sequence used to obtain the azimuthal resolution imaging for an alternative embodiment of the present invention. In this illustrative embodiment, the first gradient coil is fired with incremented amplitudes before and after echoes 1 through 5, while the second gradient coil is fired with incremented amplitudes before and after echoes 6 through 10. The gradient coil current amplitude is altered for each consecutive echo in the CPMG pulse sequence, so that at each consecutive echo, each segment is rotated by a different angle.

The echo amplitudes with respect to the second series of gradient pulse amplitudes are analyzed using Fourier transforms, which results in an image with five bins. The NMR signal intensities from the various bins correspond to either individual zones or combinations of the zones of the formation located around the NMR tool.

Figure 16:
FIG. 16 is a table showing NMR signal intensities resulting from the second gradient pulse sequence grouped in five bins, in accordance with one embodiment of the invention.

FIG. 16 is a table showing how the NMR signal intensities resulting from the second gradient pulse sequence can be grouped in five bins corresponding to zone 2, zones 1 and 3, zones 8 and 4, zones 7 and 5, and zone 6, respectively. Zones 2 and 6 can be individually distinguished since they each are in a bin by themselves. Again, it is important to note that the various zones represent differing azimuthal segments within the formation with differing azimuthal angles, for example, the area of zone 2 in FIG. 16 will have a differing azimuthal angle of coverage than the area of zone 2 in FIG. 13. It is possible for the formation coverage of zone 1 in FIG. 13 to overlap the formation coverage of zone 2 in FIG. 16, however, the ability to determine the NMR signal intensities of two adjacent zones, even with an overlap of areas, can be beneficial in providing formation data with greater azimuthal resolution. For example, the zone 1 as described above relating to FIGS. 12 and 13 provides data for an area with an average azimuthal angle in relation to a first gradient coil, while the zone 2 as described above relating to FIGS. 15 and 16 provides data for an area (part of which overlaps with zone 1 from FIG. 13) having a different average azimuthal angle in relation to the first gradient coil. The difference in the average azimuthal angles can be considered the formation resolution between these two sets of data, but does not provide this level of formation resolution around the entire wellbore circumference.

Figure 17:
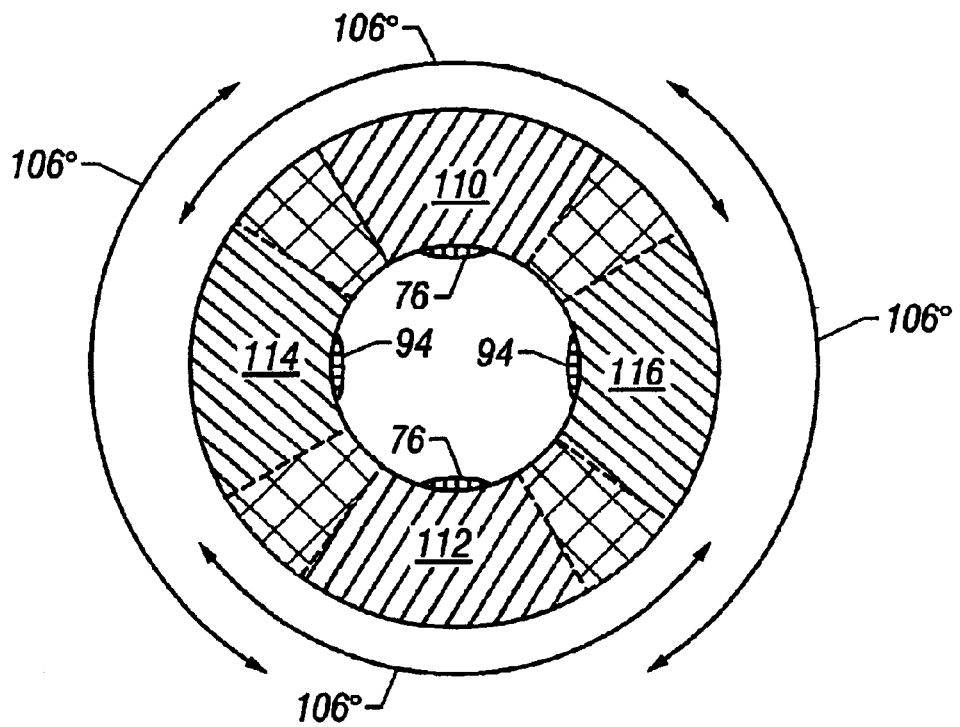
FIG. 17 illustrates an embodiment of the present invention.

FIG. 17 illustrates an embodiment of the present invention in which azimuthal imaging can be obtained with two gradient coils 76, 94 that are located perpendicular to each other (i.e., 90° spacing from each other). The analysis of the NMR signals relating to the first gradient coil 76 with five phase encoding gradients provides data representing a top zone 110 and a bottom zone 112, each having an azimuthal resolution covering approximately 106°. The analysis of the NMR signals relating to the second gradient coil 94 with five phase encoding gradients provides data representing a left zone 114 and a right zone 116, each having an azimuthal resolution covering approximately 106°. Other azimuthal resolutions can be obtained by altering the number of phase encoding gradients that are used, for example, the azimuthal resolution can be reduced from approximately 106° to approximately 83° by using eight phase encoding gradients rather than the five gradients discussed above.

Azimuthal images like those that can be obtained from a second gradient coil located at 45° resolution from the first gradient coil can also be obtained with two gradient coils oriented perpendicular (i.e., 90°) to each other as illustrated in FIG. 17. The first phase encoding gradient coil 76 can be fired by itself, as described above, to produce a first set of binned results corresponding to the groupings of a first set of azimuthal zones. During the firing of the second gradient coil 94, the first gradient coil 76 can also be fired, both gradient coils fired at approximately the same time and having approximately the same amplitude. The result of the simultaneous firing of both gradient coils 76, 94 produces a gradient field that is comparable to a field that would have been created by a single gradient coil located between the two gradient coils (i.e., at an azimuthal position 45° from the first coil). The simultaneous firing of both gradient coils replicates the effects of a hypothetical single gradient coil located at 45° spacing from the first gradient coil and results in a second set of five different bins of data corresponding to the groupings of a second set of azimuthal zones. The orientation of the magnetic field generated by the simultaneous firing of both gradient coils can be varied by changing the relative current amplitudes of the two gradient coils as they are fired together, thereby obtaining azimuthal resolutions approximately equivalent to a hypothetical gradient coil, located at an equivalent gradient coil phase angle, without physically altering the location of the gradient coils. The cumulative magnetic field gradient pulse effect of the two simultaneously fired gradient coils defines the equivalent gradient coil phase angle, (i.e., the location where a single hypothetical gradient coil would be located to produce an equivalent gradient pulse).

Depending upon the geometric design of the gradient coils 76, 94, the duration, and the strength of the current pulse applied to the coil 76, 94, the spins in a sensitive region (e.g., one zone) will phase encode in one of the following manners: radial phase encoding, azimuthal phase encoding, axial phase encoding, or incomplete phase encoding. Firing a current of sufficient magnitude through the gradient coils causes the additional phase shift of the spins subjected to the magnetic field gradient of the coil to be distributed over a range from −180° to 180° and possibly vary by several multiples of 360° over the sensitive region. For radial, axial, and azimuthal phase encoding, a varying additional phase angle is generated so that the response of spins in a sensitive region (e.g., one quadrant) averages to zero.

Azimuthal Phase Encoding (Dipole)

Figure 18:
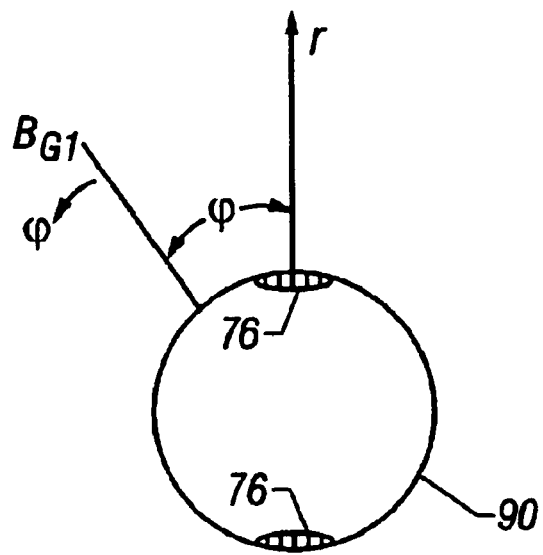
FIG. 18 illustrates the radial and angular directions of an embodiment of the present invention.
Figure 19:
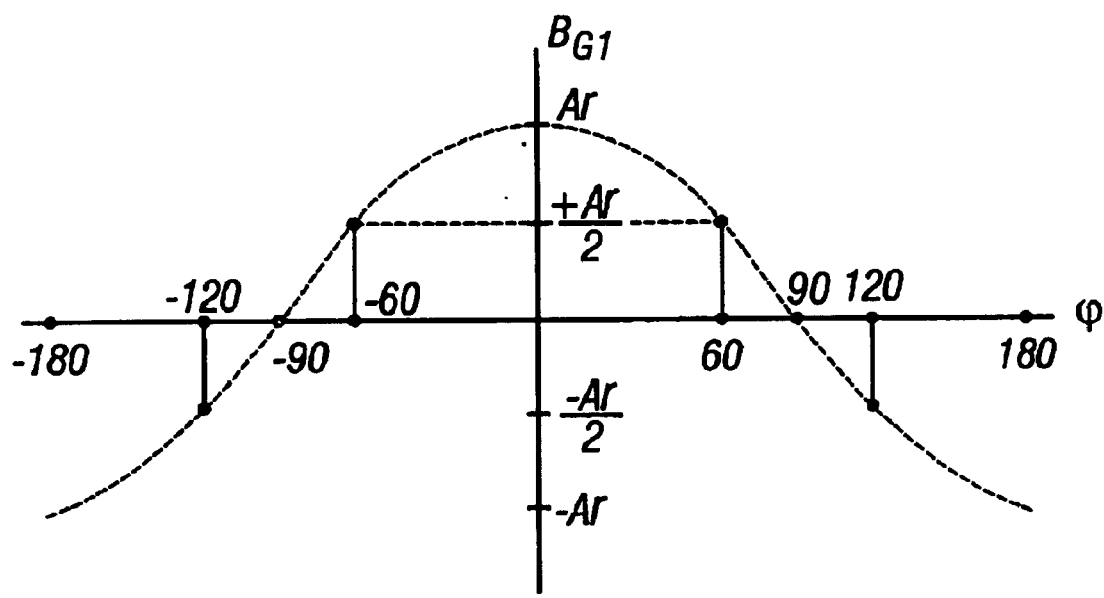
FIG. 19 graphically illustrates the amplitude of the radial component as a function of the azimuthal angle.

FIG. 18 illustrates a tool 90 with a dipole gradient coil 76 having a magnetic field pattern given by:

$$B_{G_1}(r,\phi) = A_r \cos\phi \hat{r} + A_\phi \sin\phi \hat{\phi}$$

where $A_r$ is the amplitude of the field along the radial (r) direction, $A_\phi$ is the amplitude along the azimuthal ($\phi$)

direction, and ϕ is the azimuthal angle. The magnetic field gradient is oriented circumferentially into the investigation region relative to the wellbore. The radial component of the field is responsible for phase-encoding the nuclear spins and is graphically illustrated in FIG. 19, where the amplitude of the radial component is shown as a function of the azimuthal angle ϕ.

The alteration of the nuclei spin rotation by the phase encoding gradient pulses is not equal across all of the azimuthal angles. The gradient magnetic field comprises a maximum amplitude at ϕ=0; reduces to approximately half amplitude at +60° and −60°; is approximately zero at +90° and −90°; is approximately negative one half amplitude at +120° and −120°; and is a negative maximum amplitude at +180° and −180°.

Figure 20:
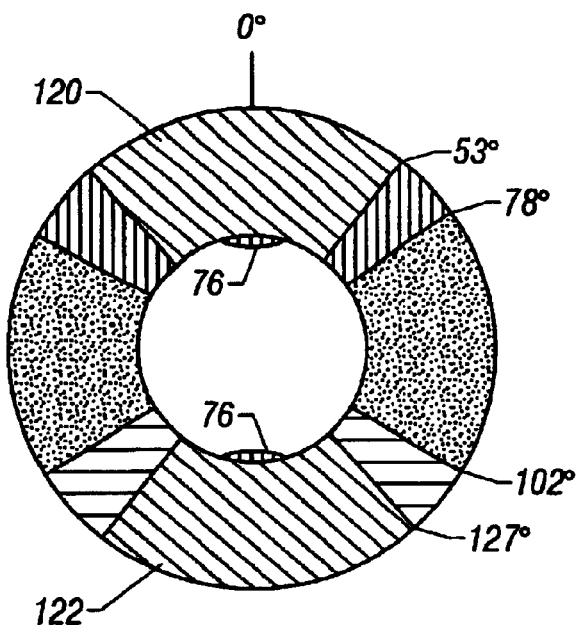
FIG. 20 illustrates an embodiment of the present invention.

For example, an NMR image utilizing five phase encoding gradient pulses can result in five bins of data, relating to various combinations of the eight zones of interest within the formation. The angular coverage of each zone can be different, since the gradient magnetic field strength varies as the cosine of the azimuthal angle. A graphical illustration of the zones with this particular phase encoding is shown in FIG. 20. Two of the data bins will provide the spin densities directly for the top segment 120 and bottom segment 122, while the other bins will contain combinations of the spin densities of the other segments.

The azimuthal resolution that can be obtained depends on the number of independent phase encoding gradient pulses utilized. The azimuthal resolution obtained from five phase encoding gradients provides eight zones as shown in FIG. 20 and provides a top quadrant with an azimuthal angle of approximately 106° (+53° to −53°). Increased azimuthal resolution can be obtained with increased numbers of phase encoding gradients.

Radial Phase Encoding

Figure 21:
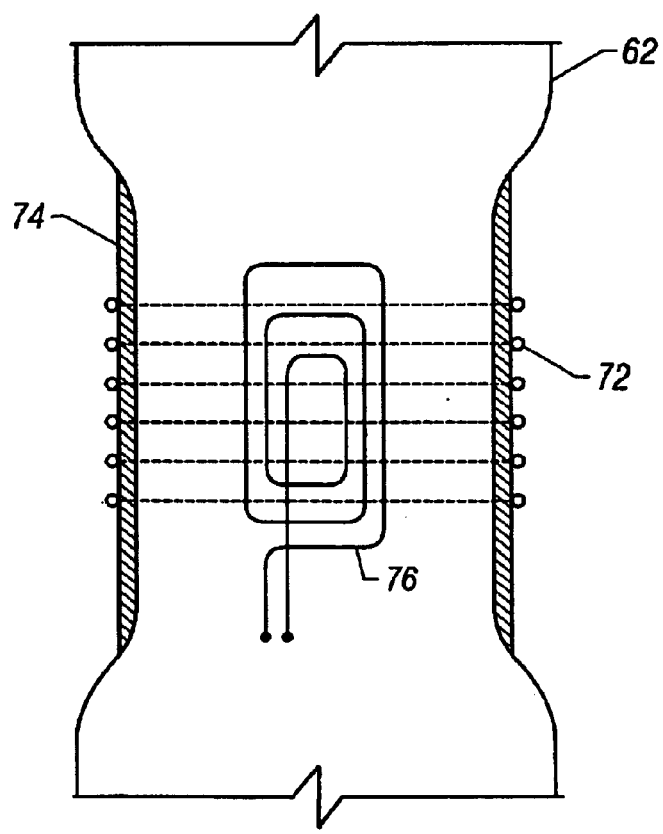
FIG. 21 illustrates an alternate embodiment of the present invention.
Figure 22:
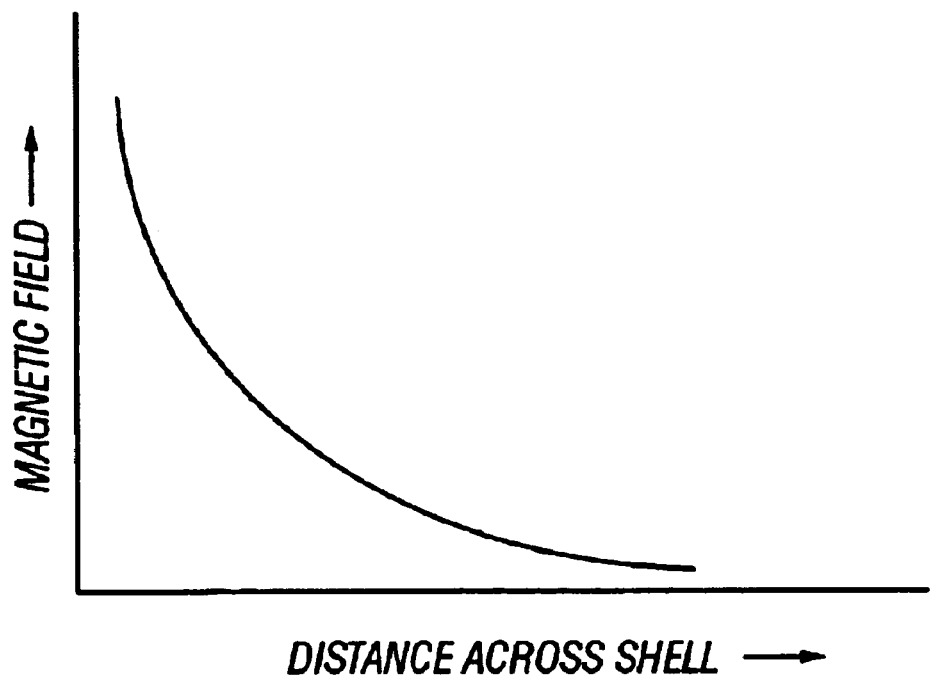
FIG. 22 graphically illustrates the magnetic field profile versus radial distance of an embodiment of the present invention.
Figure 23:
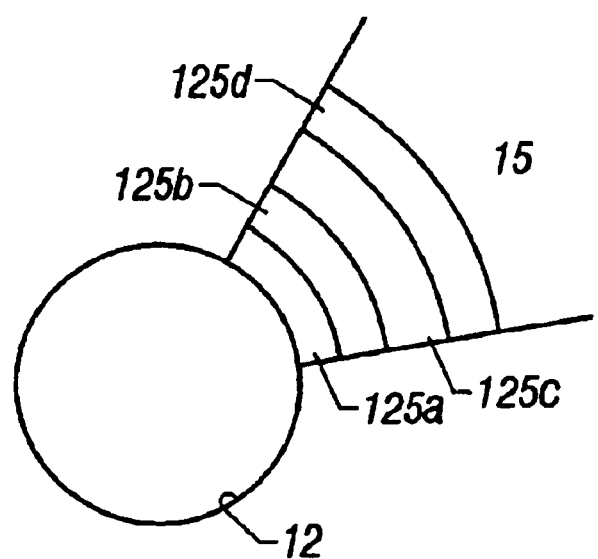
FIG. 23 illustrates the partitioning of a formation into radial segments in one embodiment of the present invention.

FIG. 21 illustrates a gradient coil 76 with geometry useful for radial phase encoding. This is achieved by generating a strong gradient field with a single coil so that the additional phase due to the field of the gradient coil 76 varies within the thickness (i.e., shell) of the sensitive region by at least π, (wherein π radians is equivalent to 180°). FIG. 22 graphically depicts the magnetic field strength across the shell. FIG. 23 illustrates a wellbore 12 and the partitioning of a section of formation 15 into a plurality of radially segmented sections 125a–125d. The magnetic gradient field is oriented radially into the investigation region relative to the wellbore 12. In the portion of the shell close to the gradient coil, spins rotate faster than spins toward an outside portion of the shell. When the NMR signals are analyzed utilizing Fourier transforms, data can be grouped into a plurality of bins, the content of each bin representing the measured signals from at least one of the radially segmented sections. The binned data can then be mapped to one or more radially segmented formation sections of the wellbore.

Axial Phase Encoding

Figure 24:
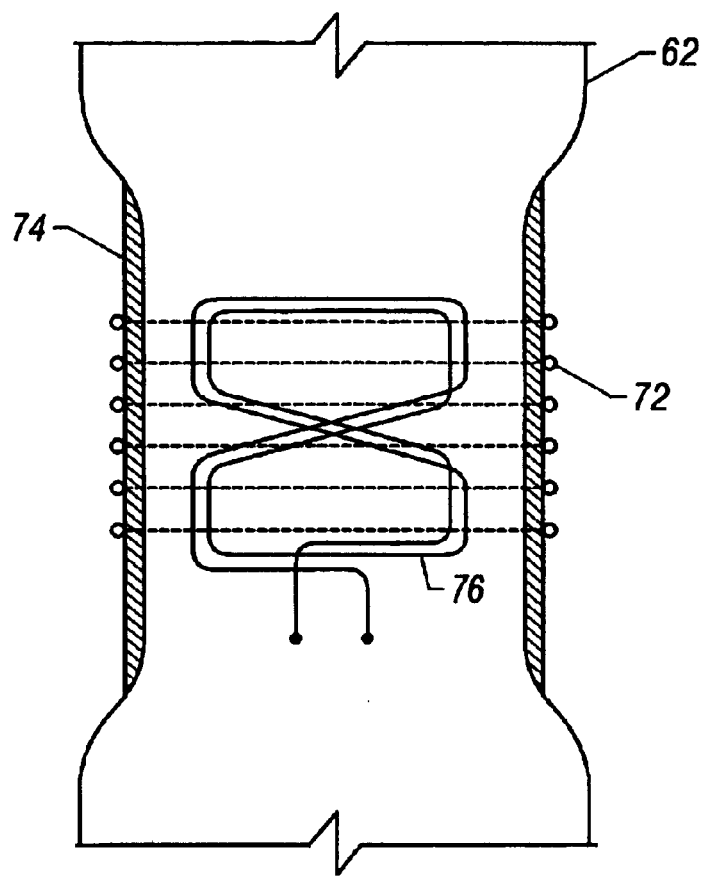
FIG. 24 illustrates an alternate embodiment of the present invention.
Figure 25:
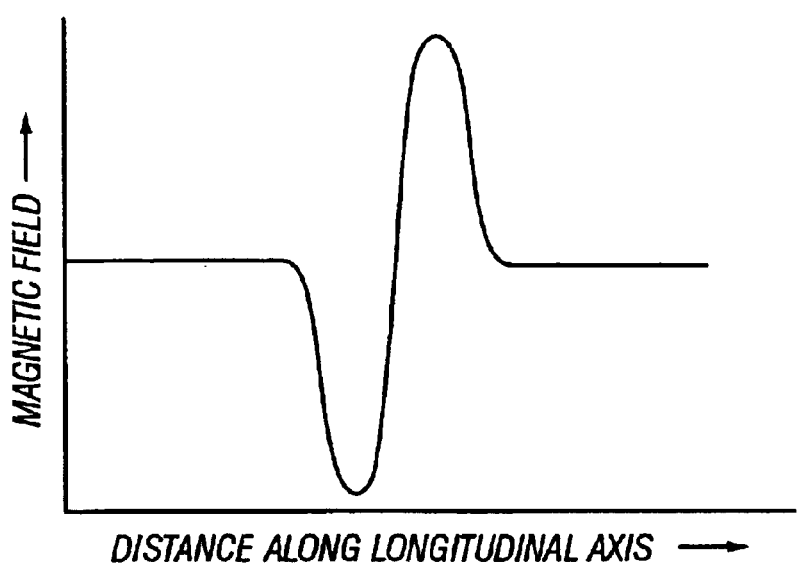
FIG. 25 graphically illustrates the magnetic field profile versus axial distance of an embodiment of the present invention.
Figure 26:
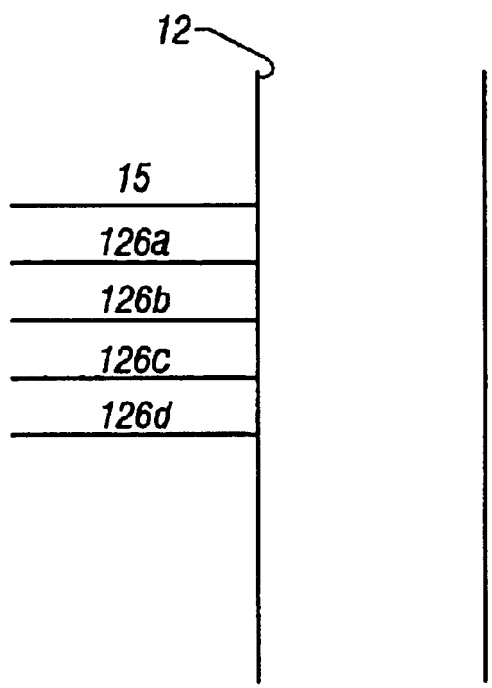
FIG. 26 illustrates the partitioning of a formation into axial segments in one embodiment of the present invention.
Figure 27:
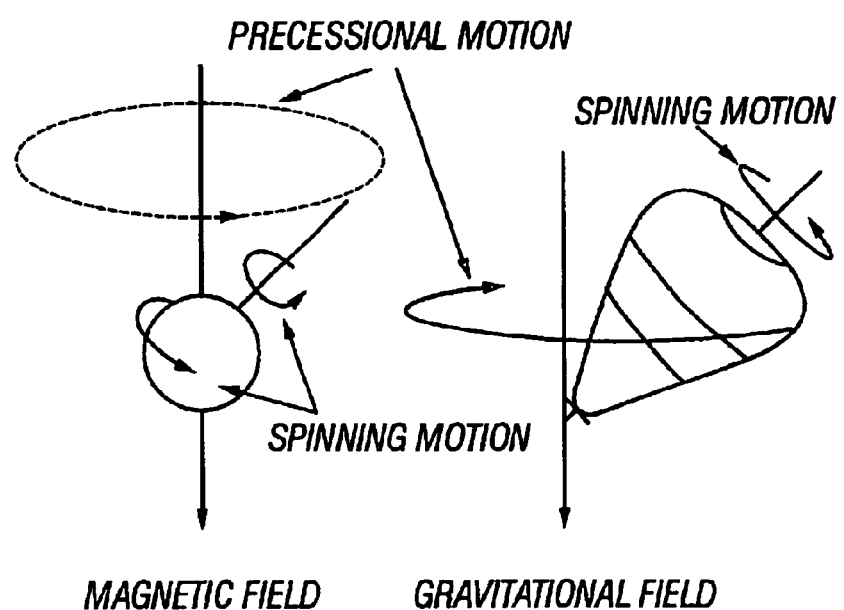
FIG. 27 illustrates the concepts of nuclei spinning motion and precessional motion within a three-dimensional space.
Figure 28:
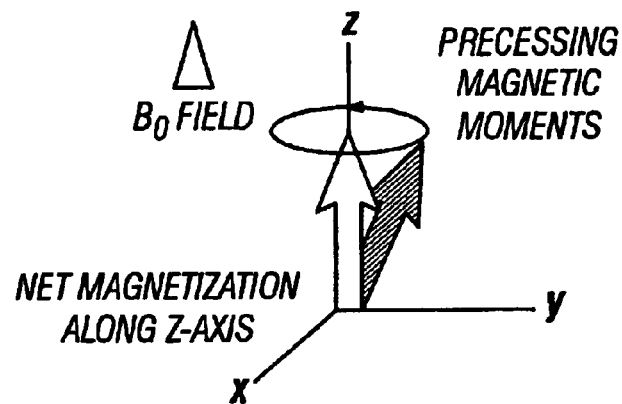
FIG. 28 illustrates a directionally imposed static magnetic field within a three-dimensional space.
Figure 29:
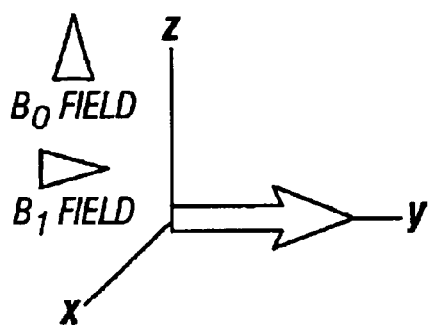
FIG. 29 illustrates the concept of spin tipping and an applied transverse magnetic field.
Figure 30:
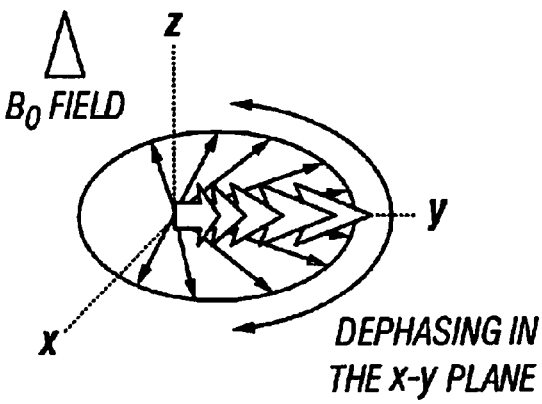
FIG. 30 illustrates the concept of dephasing of nuclei precessing around a static magnetic field.

Axial phase encoding can be used to obtain greater axial resolution, FIG. 24 illustrates an example of gradient coil geometry useful for axial phase encoding. The phase angle varies along the longitudinal axis of the tool. FIG. 25 depicts the magnetic field strength along the length of the tool. FIG. 26 illustrates a wellbore 12 and the partitioning of a section of formation 15 into a plurality of axially segmented sections 126a–126d. The magnetic gradient field is oriented axially into the investigation region relative to the wellbore 12. When the NMR signals are analyzed utilizing Fourier transforms, data can be grouped into a plurality of bins, the content of each bin representing the measured signals from at least one of the axially segmented sections. The binned data can then be mapped to one or more axially segmented formation sections of the wellbore.

The present invention enables improved resolution imaging of a formation using a phase encoding means that produces altered NMR signals. These altered NMR signals can be analyzed utilizing Fourier transforms. Applying a pulsed magnetic field gradient within a particular direction, before the NMR signal acquisition, can alter the nuclei spins within the investigation region in that particular phase encoding direction. This gradient pulse is stepped through a series of differing amplitudes on subsequent excitations, so that the phase of the NMR signals along that direction are also incremented. Because of the position dependent nature of the NMR signal phase increments, the signals can be resolved by utilizing Fourier transforms along that direction. U.S. Pat. No. 6,326,784 assigned to Schlumberger Technology Corporation discloses one means of utilizing Fourier transforms of NMR signals that can be grouped within bins, the binned data representing groupings of NMR signals obtained from one or more azimuthal zones around the NMR tool.

The NMR signal, $f(G_\phi)$ for a particular applied gradient strength G is given by the following equation:

$$f(G_\phi) = \int f(\phi) e^{-i\gamma \int_0^t G G_\phi \phi dt} d\phi$$

where $f(\phi)$ is the azimuthal formation spin density, $t_G$ is the time duration of the phase encoding gradient, $\phi$ is the azimuthal angle, and $\gamma$ is the gyromagnetic ratio for the particular NMR sensitive nuclei.

A term, k-space, is used in NMR imaging and it is defined as the following formula:

$$k_\phi = \gamma \int_0^t G_\phi dt$$

The k-space defines the domain in which the raw magnetic resonance measurements are obtained. The amplitude of the phase encoding gradient is typically incremented with each excitation and correspondingly the phase of the NMR spins also increment. To satisfy the Nyquist requirement, the phase of spins is incremented by π radians in the imaged volume with each measurement.

The NMR signal for a particular $k_\phi$ value can be written as:

$$f(k_\phi) = \int f(\phi) e^{-ik\phi} d\phi$$

The azimuthal formation spin density, which can also be referred to as the formation image $f(\phi)$, is the Fourier transform of $f(k_\phi)$, which is written as:

$$f(\phi) = \int f(k_\phi) e^{ik\phi} dk$$

The order in which the k-space is sampled is commonly either sequential or centric, although other sampling orders can also be used. In sequential ordering the phase encoding gradients are incremented linearly. In centric ordering, the phase encoding gradients are alternatively varied in the positive and negative direction. The signal to noise ratio of the NMR image is largely determined by the low frequency components of the NMR signal (which are located close to a central position within the k-space). The high frequency components determine the sharpness of the NMR image (located at the peripheral region within the k-space).

In one embodiment of the present invention, the method comprises applying a series of magnetic field gradients to a spin-echo series such that consecutive echoes are altered by a magnetic field gradient of differing amplitudes. The magnetic field gradient will effect the nuclei within the formation differently, depending on the nuclei position relative to the magnetic field gradient. The series of altered echoes can be detected and analyzed with respect to the differing magnetic field gradient amplitudes and segmented in relation to the azimuthal, radial or axial position relative to the wellbore. Utilizing this method, formation NMR responses can be determined for various segments within the formation.

Embodiments of the invention can be utilized during the drilling of the wellbore for early formation evaluations, while other embodiments can be used in existing wellbores and deployed by wireline means. The invention can be used in conjunction with other instruments and tools, providing flexibility that can be used at the discretion of the operator.

In further embodiments of the invention, multiple series of altered echoes, either from additional runs of a single gradient coil or the use of multiple gradient coils, can be generated, collected and analyzed. By analyzing multiple series of altered echoes, an image of the formation having a particular resolution (e.g., degree of angular segment) can be developed. When coupled with a MWD apparatus, the various segments of the formation can be translated into surface directional coordinates for use in formation evaluation and reservoir management.

Thus, the present invention enables the generation and imaging of NMR formation responses. Through use of the present invention, the resolution of the NMR imaging can be determined and controlled, thereby providing improved knowledge of the formation properties and assisting with an overall formation evaluation and reservoir management effort. The ability of the present invention to obtain formation properties without the use of radioactive sources reduces potential environmental concerns that accompany various other methods of formation evaluation.

The foregoing descriptions of alternate embodiments of the present invention have been presented for purposes of illustration and description. It is not intended to be exhaustive or limit the invention to the precise form disclosed. With the acquisition of formation imaging having improved resolution, the present invention may perform be useful in determining various formation properties, e.g., porosity, bound fluid volume (BFV), and permeability measurements. It is also possible to perform azimuthal magnetic resonance imaging, which is useful for interpreting heterogenous formations and performing geologically based steering in deviated or horizontal boreholes. Obviously, many modifications and variations will be apparent to those skilled in the art. For example, the functionality of the MWD tool 52 may also be performed in the LWD tool 50 or divided between the MWD 52 and LWD 50 tools. Also, with a wireline tool, the gradient coil(s) may be located on a pad connected to the tool. Those skilled in the art will appreciate that the method and gradient coil(s) of the subject invention can be useful for eliminating the magnetic resonance signal of the borehole fluids, obtaining axially resolved NMR measurements, or NMR measurements with improved vertical resolution. For example, the length of the recessed area 70 along the longitudinal axis of the borehole can define the axial extent of an investigation region. A gradient coil or a plurality of gradient coils can be oriented, at known positions along the longitudinal axis of the borehole, within the recessed area 70. A current pulse applied to the gradient coil(s) will phase encode the spins in an axial segment of the formation. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the accompanying claims and their equivalents.

What is claimed is:

1. A method for nuclear magnetic resonance imaging of an investigation region of formation surrounding a wellbore, comprising the steps of:

generating a static magnetic field in the investigation region of formation surrounding a wellbore;

producing an rf magnetic field in the investigation region;

applying a series of non-linear magnetic field gradients to phase encode nuclei spins within the investigation region, wherein the strength of the magnetic field gradient applied is different from at least one previously applied magnetic field gradient within the series; and detecting nuclear magnetic resonance signals from the investigation region resulting from the series of magnetic field gradients.

2. The method of claim 1, further comprising the step of mapping the signals to one or more angular segment of the formation around the wellbore.

3. The method of claim 1, further comprising the step of mapping the signals to one or more radial segment of the formation around the wellbore.

4. The method of claim 1, further comprising the step of mapping the signals to one or more axial segment of the formation around the wellbore.

5. The method of claim 1, further comprising the step of applying a static magnetic field circumferentially around the wellbore and into the investigation region.

6. The method of claim 1, further comprising the step of applying a RF magnetic field circumferentially around the wellbore and into the investigation region.

7. The method of claim 1, wherein each of the magnetic field gradients of the series of magnetic field gradients is oriented circumferentially into the investigation region relative to the wellbore.

8. The method of claim 1, wherein the series of magnetic field gradients are oriented radially into the investigation region relative to the wellbore.

9. The method of claim 1, wherein the series of magnetic field gradients are oriented axially into the investigation region relative to the wellbore.

10. The method of claim 1, further comprising the step of inducing a plurality of spin-echo signals from selected nuclei in the investigation region of the formation.

11. The method of claim 10, further comprising the step of canceling the applied magnetic field gradient prior to applying a magnetic field gradient for the next spin-echo signal.

12. The method of claim 1, further comprising the step of generating a sequence of pulses and spin-echoes, including gradient pulse, from a single gradient coil, that provides an azimuthally resolved image of a portion of the formation.

13. The method of claim 12, wherein during a single pulse sequence, the step of generating a sequence of pulses and spin-echoes comprises the steps of:

i) during a first time period, applying a first RP pulse and a first gradient pulse in the investigation region and measuring the generated signals in the investigation region;

ii) canceling the first gradient pulse;

iii) during a second time period, applying a second RF pulse and a second gradient pulse in the investigation region and measuring the generated signals in the investigation region, wherein the second gradient pulse has an amplitude that in incremented from the first gradient pulse.

14. The method of claim 1, further comprising the step of generating a sequence of pulses and spin-echoes that provides a radially resolved image of a portion of the formation.

15. The method of claim 1, further comprising the step of generating a sequence of pulses and spin-echoes that provides an axially resolved image of a portion of the formation.

16. The method of claim 1, further comprising the steps of generating a first pulse sequence comprising a plurality of phase alternated RF pulses, a first set of incremented phase altering gradient pulses and a first set of spin-echoes end generating a second pulse sequence comprising a plurality of phase alternated RF pulses, a second set of incremented phase altering gradient pulses, and a second set of spin-echoes, the first and second pulse sequences being sufficient to derive an azimuthal image of the formation surrounding the wellbore.

17. The method of claim 16, wherein the first set of incremented phase altering gradient pulses is generated from a first gradient coil and the second set of incremented phase altering gradient pulses is generated from a second gradient coil, wherein the second gradient coil is angularly spaced from the first gradient coil within the wellbore, defining a gradient coil phase angle.

18. The method of claim 17, wherein the image of the formation mapped from the unclear magnetic resonance signals from the investigation region has an azimuthal resolution substantially equal to the gradient coil phase angle.

19. The method of claim 1, further comprising the step of processing the detected nuclear magnetic resonance signals to optimize the formation image.

20. The method of claim 1, further comprising the step of detecting the nuclear magnetic resonance signals while drilling into the formation.

21. The method of claim 1, further comprising the steps of detecting the detected nuclear magnetic resonance signals, and partitioning the detected signals into a plurality of bins.

22. The method of claim 21, further comprising the step of partitioning a cross-section of the formation into a plurality of angular distance segments wherein each bin represents the measured signals from at least one of the angular distance segments.

23. The method of claim 1, further comprising the steps of solving a series of Fourier transforms of the detected nuclear magnetic resonance signals, and partitioning the Fourier transforms into a plurality of bins.

24. The method of claim 23, further comprising the step of partitioning a cross-section of the formation into a plurality of angular distance segments, wherein each bin represents the measured signals from at least one of the angular distance segments.

25. The method of claim 24, wherein the strength of the magnetic field gradient of greatest amplitude is chosen so that, when the magnetic field gradient is applied, it is at least strong enough to induce a phase difference between adjacent angular distance segments of at least 180 degrees.

26. The method of claim 23, further comprising the step of partitioning a portion of the formation into a plurality of radial distance segments, wherein each bin represents the measured signals from at least one of the radial distance segments.

27. The method of claim 23, further comprising the step of partitioning a portion of the formation into a plurality of axial distance segments, wherein each bin represents the measured signals from at least one of the axial distance segments.

28. The method of claim 1, further comprising the steps of providing a plurality of gradient means positioned around the circumference of a logging device and selecting at least one of the gradient means to apply the magnetic field gradient to the formation.

29. The method of claim 28, further comprising the simultaneous application of gradient pulses from two or more gradient means to phase encode nuclei spins within the investigation region.

30. The method of claim 29, further comprising controlling the amplitudes of the two or more gradient means to produce a cumulative gradient pulse effect, and defining an equivalent gradient coil phase angle.

31. The method of claim 30, further comprising the steps of solving at least one Fourier transform of the detected nuclear magnetic resonance signals, and partitioning the at least one Fourier transform solution into a plurality of bins.

32. The method of claim 31, further comprising the step of partitioning a cross-section of the formation into a plurality of angular distance segments, wherein each bin represents the measured signals from at least one of the angular distance segments.

33. The method of claim 1, further comprising the step of azimuthally changing the phase of nuclei spins within the investigation region.

34. The method of claim 1, further comprising the step of radially changing the phase of nuclei spins within the investigation region.

35. The method of claim 1, further comprising the step of axially changing the phase of nuclei spins within the investigation region.

36. A method for measuring a nuclear magnetic resonance property in an investigation region of earth formations surrounding a wellbore, comprising the steps of:
   a) drilling a wellbore in the formation with a logging-while-drilling device;
   b) measuring the nuclear magnetic resonance properties of at least one formation while drilling the wellbore, comprising the steps of:
      i) applying a static magnetic field circumferentially around the wellbore and into the investigation region of earth formations surrounding the wellbore as the logging device moves within the wellbore;
      ii) applying an RF magnetic field circumferentially around the wellbore and into the investigation region as the logging device moves within the wellbore;
      iii) inducing a plurality of spin-echo, signals from selected nuclei of the formation;
      iv) applying a series of non-linear magnetic field gradients to phase encode spins within the investigation region, the strength of the magnetic field gradient applied for spin-echo signal is different from previously applied magnetic field gradients within the series; and
      v) detecting nuclear magnetic resonance signals from the investigation region.

37. The method of claim 36, further comprising the step of generating a first pulse sequence comprising a plurality of phase alternated RF pulses and spin-echoes and a first series of magnetic field gradients, and generating a second pulse sequence comprising a plurality of phase alternated RF pulses and spin-echoes and a second series of magnetic field gradients, tire first and second pulse sequences being sufficient to derive an azimuthal image of the formation surrounding the wellbore.

38. The method of claim 36, wherein during a single pulse sequence, the step of generating a sequence of pulses and spin-echoes comprises the steps of:
   i) during a first time period, applying a first RF pulse and a first gradient pulse in the investigation region and measuring the generated signals in the investigation region;
   ii) canceling the first gradient pulse;
   iii) during a second time period, applying a second RF pulse and a second gradient pulse in the investigation region and measuring the generated signals in the investigation region, wherein the second gradient pulse has an amplitude that is different from the first gradient pulse.

39. The method of claim 38, wherein the step of generating a pulse sequence further comprises the step of applying a fixed wait time between applying the RF pulse and the gradient pulse.

40. The method of claim 38, wherein the step of generating a pulse sequence further comprises the step of applying a variable wait time between applying the RF pulse and the gradient pulse.

41. The method of claim 36, further comprising the simultaneous application of gradient pulses from two or more gradient means to diphase nuclei spins within the investigation region.

42. The method of claim 41, further comprising controlling the amplitudes of the two or more gradient means to produce a cumulative gradient pulse effect.

43. The method of claim 42, further comprising the steps of solving a series of Fourier transforms of the detected nuclear magnetic resonance signals, and partitioning the Fourier transforms into a plurality of bins.

44. The method of claim 43, further comprising to step of partitioning a cross-section of the formation into a plurality of angular distance segments, wherein to content of each bin represents the measured signals from at learnt one of the angular distance segments.

45. The method of claim 44, further comprising the step of mapping the measured signals to one or more angular segment of the formation around the wellbore.

46. The method of claim 45, wherein the strength of the magnetic field gradient of greatest amplitude is chosen so that, when to magnetic field gradient is applied, it is at least strong enough to induce a phase difference between adjacent angular distance segments of at least 180 degrees.

47. The method of claim 43, further comprising the step of partitioning a section of the formation into a plurality of radially segmented formation sections, wherein the content of each bin represents the measured signals from at least one of the radially segmented formation sections.

48. The method of claim 47, further comprising the step of mapping the measured signals to one or more radially segmented formation sections of the wellbore.

49. The method of claim 43, further comprising the step of partitioning a section of the formation into a plurality of axial distance segments, wherein the content of each bin represents the measured signals from at least one of the axial distance segments.

50. The method of claim 49, further comprising the step of mapping the measured signals to one or more axial distance segments of the wellbore.

51. A method for measuring a nuclear magnetic resonance property in an investigation region of earth formations surrounding a borehole, comprising the steps of:
   a) positioning a logging device in the borehole;
   b) measuring the nuclear magnetic resonance properties in the investigation region of earth formations surrounding the borehole, comprising the steps of:
      i) applying a static magnetic field circumferentially around the borehole and into the investigation region;
      ii) applying an RF magnetic field circumferentially around the borehole;
      iii) inducing a plurality of spin-echo signals from selected nuclei of the formation;
      iv) applying a series of non-linear magnetic field gradients to phase encode spins in a portion of the investigation region wherein the strength of the magnetic field gradient applied for each spin-echo signal is altered from previously applied magnetic field gradients within the series; and
      v) detecting nuclear magnetic resonance signals from the investigation region;
   c) analyzing the nuclear magnetic resonance signals utilizing Fourier transform analysis;
   d) partitioning the Fourier transform analysis results into a plurality of bins;
   e) partitioning a cross-section of the formation into a plurality of angular distance segments, wherein each bin represents the measured signals from at least one of the angular distance segments; and
   f) mapping the signals from at least one bin to at least one angular segment of the formation around the wellbore.

52. The method of claim 51, further comprising the step of azimuthally changing the phase of nuclei spins within the investigation region.

53. The method of claim 51, further comprising the step of radially changing the phase of nuclei spins within the investigation region.

54. The method of claim 51, further comprising the step of axially changing the phase of nuclei spins within the investigation region.

55. The method of claim 51, wherein the strength of the magnetic field gradient of greatest amplitude is chosen so that, when the magnetic field gradient is applied, it is at least strong enough to induce a phase difference between adjacent angular segments of at least 180 degrees.

56. The method of claim 55, further comprising the simultaneous application of magnetic field gradient pulse from two or more gradient means to phase encode nuclei spins within the investigation region.

57. The method of claim 56, further comprising controlling the amplitudes of the two or more gradient means to produce a cumulative gradient pulse effect, and thereby defining an equivalent gradient coil phase angle.

58. A method for measuring a nuclear magnetic resonance property in an investigation region of earth formations surrounding a borehole, comprising the steps of:
   a) positioning a logging device in the borehole;
   b) measuring the nuclear magnetic resonance properties in the investigation region of earth formations surrounding the borehole, comprising the steps of:
      i) applying a static magnetic field circumferentially around the borehole and into the investigation region;
      ii) applying an RF magnetic field circumferentially around the borehole;
      iii) inducing a plurality of spin-echo signals from selected nuclei of the formation;
      iv) applying a series of non-linear magnetic field gradients to phase encode spins in a portion of the investigation region wherein the strength of the magnetic field gradient applied for each spin-echo signal is altered from previously applied magnetic field gradients within the series; and v) detecting nuclear magnetic resonance signals from the investigation region;

c) analyzing the nuclear magnetic resonance signals utilizing Fourier transform analysis;

d) partitioning the Fourier transform analysis results into a plurality of bins;

e) partitioning a cross-section of the formation into a plurality of radial distance segments, wherein each bin represents the measured signals from at least one of the radial distance segments; and f) mapping the signals from at least one bin to at least one radial segment of the formation around the wellbore.

59. A method for measuring a nuclear magnetic resonance property in an investigation region of earth formations surrounding a borehole, comprising the steps of:

a) positioning a logging device in the borehole;

b) measuring the nuclear magnetic resonance properties in the investigation region of earth formations surrounding the borehole, comprising the steps of:
  i) applying a static magnetic field circumferentially around the borehole and into the investigation region;
  ii) applying an RF magnetic field circumferentially around the borehole;
  iii) inducing a plurality of spin-echo signals from selected nuclei of the formation;
  iv) applying a series of non-linear magnetic field gradients to phase encode spins in a portion of the investigation region wherein the strength of the magnetic field gradient applied for each spin-echo signal is altered from previously applied magnetic field gradients within the series; and
  v) detecting nuclear magnetic resonance signals from the investigation region;

c) analyzing the nuclear magnetic resonance signals utilizing Fourier transform analysis;

d) partitioning the Fourier transform analysis results into a plurality of bins;

e) partitioning a cross-section of the formation into a plurality of axial distance segments, wherein each bin represents the measured signals from at least one of the axial distance segments; and f) mapping the signals from at least one bin to at least one axial segment of the formation around the wellbore.

60. An apparatus for determining a nuclear magnetic resonance property in an investigation region of earth formations surrounding a wellbore, comprising:

a) a logging device moveable through the wellbore;

b) means in the logging device for applying a static magnetic field circumferentially around the wellbore and into the investigation region of earth formations surrounding the wellbore;

c) antenna means in the logging device for applying an RF magnetic field circumferentially around the borehole and into the investigation region, whereby the antenna means induces a plurality of pulse echoes and spin-echo signals from selected nuclei of the formation;

d) at least one gradient means in the logging device capable of producing a non-linear gradient magnetic field within the borehole and into the investigation region and capable of producing different strength gradient magnetic fields for each of the plurality of pulse echoes, wherein the orientation of the gradient magnetic field and the static magnetic field effects on the selected nuclei vary depending on the azimuthal position around the wellbore in relation to the gradient means; and e) means for detecting nuclear magnetic resonance signals from the investigation region.

61. The apparatus of claim 60, further comprising mini for generating a sequence of pulses and spin-echoes, including gradient pulses from a single gradient coil, that provides an azimuthally resolved nuclear magnetic resonance measurement.

62. The apparatus of claim 60, further comprising means for generating a first pulse sequence comprising a plurality of phase alternated RF pulses and spin-echoes and means for generating a second pulse sequence comprising a plurality of phase alternated RF pulses, at least one gradient pulse, and spin-echoes, the first and second pulse sequences being sufficient to derive an azimuthal image of the formation surrounding the wellbore.

63. The apparatus of claim 60, wherein the at least one gradient means comprises two gradient coils positioned approximately perpendicular to each other.

64. The apparatus of claim 60, wherein each gradient coil is capable of producing a variable strength gradient magnetic field into the investigation region.

65. An apparatus for determining a nuclear magnetic resonance property in an investigation region of earth formations surrounding a wellbore, comprising:

a) a logging device moveable through the wellbore;

b) means in the logging device for applying a static magnetic field circumferentially around the wellbore and into the investigation region of earth formations surrounding the wellbore;

c) antenna means in the logging device for applying an RF magnetic field circumferentially around the borehole and into the investigation-region, whereby the antenna means induces a plurality of pulse echoes and spin-echo signals from selected nuclei of the formation;

d) at least one gradient means in the logging device capable of producing a non-linear gradient magnetic field within the borehole and into the investigation region and capable of producing different strength gradient magnetic fields for each of the plurality of pulse echoes, wherein the orientation of the gradient magnetic field and the static magnetic field effects on the selected nuclei vary depending on the radial position within the formation in relation to the gradient means; and e) means for detecting nuclear magnetic resonance signals from the investigation region.

66. The apparatus of claim 65, further comprising means for generating a sequence of pulses and spin-echoes that provides a radially resolved nuclear magnetic resonance measurement.

67. An apparatus for determining a nuclear magnetic resonance property in an investigation region of earth formations surrounding a wellbore, comprising:

a) a logging device moveable through the wellbore;

b) means in the logging device for applying a static magnetic field circumferentially around the wellbore and into the investigation region of earth formations surrounding the wellbore;

c) antenna means in the logging device for applying an RF magnetic held circumferentially around the borehole and into the investigation region, whereby the antenna means induces a plurality of pulse echoes and spin-echo signals from selected nuclei of the formation;

d) at least one gradient means in the logging device capable of producing a non-linear gradient magnetic field within the borehole and into the investigation region and capable of producing different strength gradient magnetic fields for each of the plurality of pulse echoes, wherein the orientation of the gradient magnetic held and the static magnetic field effects on the selected nuclei vary depending on the axial position within the wellbore in relation to the gradient means; and e) means for detecting nuclear magnetic resonance signals from the investigation region.

68. The apparatus of claim 67, further comprising means for generating a sequence of pulses and spin-echoes that provides an axially resolved nuclear magnetic resonance measurement.

69. An apparatus for determining a nuclear magnetic resonance property in an investigation region of earth formations surrounding a wellbore, comprising:

a) a logging device moveable through the wellbore;
  b) magnets within the logging device for applying a static magnetic field circumferentially around the wellbore and into the investigation region of earth formations surrounding the wellbore;
c) at least one antenna in the logging device for applying an RF magnetic field circumferentially around the borehole and into the investigation region, whereby the one or more antenna is capable of inducing a plurality of pulse echoes and spin-echo signals from selected nuclei of the formation;
d) one or more gradient coils within the logging device capable of producing a non-linear gradient magnetic field circumferentially around the borehole and into the investigation region, the gradient coils adapted to produce incrementally different strength gradient magnetic fields for each of the plurality of pulse echoes, wherein the orientation of the gradient magnetic field and the static magnetic field effects on the selected nuclei vary depending on the asimuthal position around the wellbore in relation to the gradient means; and
e) one or more antenna for detecting nuclear magnetic resonance signals from the investigation region.

70. The apparatus of claim 69, wherein the gradient coil is capable of applying a magnetic field gradient having a strength great enough to induce a phase difference of at least 180 degrees between adjacent angular distance segments in the formation.

71. The apparatus of claim 70, comprising two or more gradient coils capable of simultaneous application of magnetic field gradient pulses from two or more gradient coils to phase encode nuclei spins within the investigation region.

72. The apparatus of claim 71, wherein the two or more gradient coils are adapted to enable variable amplitudes of the magnetic field gradient pulses from the two or more gradient coils to produce a cumulative magnetic field gradient pulse effect, thereby defining an equivalent gradient coil phase angle.

73. The apparatus of claim 72, wherein the apparatus comprises two gradient coils located perpendicular to each other.

* * * * *